(12) United States Patent
Varghese et al.

(10) Patent No.: US 12,364,640 B2
(45) Date of Patent: Jul. 22, 2025

(54) UPPER BODY HUMAN TO MACHINE INTERFACE

(71) Applicants: Board of Regents, The University of Texas System, Austin, TX (US); Harmonic Bionics, Inc., Austin, TX (US)

(72) Inventors: Rohit John Varghese, Austin, TX (US); William Wu, Austin, TX (US)

(73) Assignees: Board of Regents, The University of Texas System, Austin, TX (US); Harmonic Bionics, Inc., Austin, TX (US)

(*) Notice: Subject to any disclaimer, the term of this patent is extended or adjusted under 35 U.S.C. 154(b) by 1043 days.

(21) Appl. No.: 17/230,154

(22) Filed: Apr. 14, 2021

(65) Prior Publication Data

US 2021/0315763 A1  Oct. 14, 2021

Related U.S. Application Data

(60) Provisional application No. 63/009,750, filed on Apr. 14, 2020.

(51) Int. Cl.
| | | |
|---|---|---|
| *A61H 1/02* | (2006.01) | |
| *A61F 2/58* | (2006.01) | |
| *A61F 2/78* | (2006.01) | |
| *B25J 9/00* | (2006.01) | |
| *A61F 2/54* | (2006.01) | |

(52) U.S. Cl.
CPC .......... *A61H 1/0285* (2013.01); *A61F 2/583* (2013.01); *A61F 2/78* (2013.01); *B25J 9/0006* (2013.01); *A61F 2002/543* (2013.01); *A61F 2002/7862* (2013.01); *A61H 2201/1638* (2013.01)

(58) Field of Classification Search
CPC .......... A61H 1/0285; A61F 2/583; B25J 9/006
See application file for complete search history.

(56) References Cited

U.S. PATENT DOCUMENTS

| | | | | |
|---|---|---|---|---|
| 18,021 | A * | 8/1857 | Selpho ................... | A61F 2/583 623/63 |
| 1,625,317 | A * | 4/1927 | Hodgson ................. | A61F 2/583 623/57 |
| 5,067,479 | A * | 11/1991 | Saringer ............... | A61H 1/0285 601/40 |
| 5,503,619 | A * | 4/1996 | Bonutti ................ | A61H 1/0285 601/33 |
| 5,695,453 | A * | 12/1997 | Neal ..................... | A61F 5/0118 602/46 |
| 5,848,979 | A * | 12/1998 | Bonutti .................. | A61F 5/013 482/45 |
| 6,565,563 | B1 * | 5/2003 | Agee ..................... | A61H 1/0288 606/55 |

(Continued)

OTHER PUBLICATIONS

"Cam," Wikipedia, retrieved from https://en.wikipedia.org/w/index.php?title=Cam&oldid=950803324, Apr. 13, 2020, seven pages.

(Continued)

*Primary Examiner* — LaToya M Louis
(74) *Attorney, Agent, or Firm* — Trop, Pruner & Hu, P.C.

(57) ABSTRACT

An embodiment includes an apparatus for coupling a user to a robot to provide robot-assisted physical therapy to the user. Other embodiments are described herein.

13 Claims, 20 Drawing Sheets

(56) References Cited

U.S. PATENT DOCUMENTS

| | | | | |
|---|---|---|---|---|
| 7,862,522 | B1* | 1/2011 | Barclay | A61B 5/6806 |
| | | | | 600/595 |
| 8,585,620 | B2* | 11/2013 | McBean | A61H 1/008 |
| | | | | 601/24 |
| 8,679,043 | B2* | 3/2014 | Bonutti | A61F 5/05875 |
| | | | | 602/22 |
| 9,326,909 | B2* | 5/2016 | Liu | A63B 22/00 |
| 10,646,356 | B2* | 5/2020 | Deshpande | A63B 21/4019 |
| 11,173,091 | B2* | 11/2021 | Pedrocchi | A61H 1/0285 |
| 11,224,553 | B2* | 1/2022 | Perry | A61H 1/0288 |
| 11,446,198 | B2* | 9/2022 | Ou | A63B 21/4019 |
| 11,464,450 | B2* | 10/2022 | Huang | G06F 3/014 |
| 11,465,034 | B2* | 10/2022 | Sharp | A41F 1/06 |
| 11,690,774 | B2* | 7/2023 | Bhugra | G06F 3/014 |
| | | | | 601/5 |
| 12,179,356 | B2* | 12/2024 | Desai | B25J 9/1633 |
| 2003/0223844 | A1* | 12/2003 | Schiele | A63B 23/12 |
| | | | | 414/5 |
| 2007/0100266 | A1* | 5/2007 | Hargrave | A61F 5/012 |
| | | | | 602/5 |
| 2009/0030353 | A1* | 1/2009 | Bonutti | A61H 1/0274 |
| | | | | 601/5 |
| 2010/0152628 | A1* | 6/2010 | Kaiser | A61H 1/0285 |
| | | | | 601/5 |
| 2010/0280423 | A1* | 11/2010 | Kawakami | A61H 1/0277 |
| | | | | 601/33 |
| 2012/0059291 | A1* | 3/2012 | Nguyen | A61H 1/0288 |
| | | | | 601/40 |
| 2013/0030327 | A1* | 1/2013 | Zhang | A61F 5/0102 |
| | | | | 600/587 |
| 2014/0039372 | A1* | 2/2014 | Blue | A61F 5/0118 |
| | | | | 602/21 |
| 2014/0052039 | A1* | 2/2014 | Summit | A61F 5/0118 |
| | | | | 602/21 |
| 2015/0081036 | A1* | 3/2015 | Nakanishi | A61H 1/0266 |
| | | | | 623/24 |
| 2015/0148728 | A1* | 5/2015 | Sallum | A61F 5/013 |
| | | | | 602/22 |
| 2015/0190246 | A1* | 7/2015 | Ryu | A61H 1/0285 |
| | | | | 74/89.22 |
| 2016/0081834 | A1* | 3/2016 | Bonutti | A61F 5/013 |
| | | | | 602/22 |
| 2016/0229635 | A1* | 8/2016 | Summer | A61F 5/05875 |
| 2016/0296345 | A1* | 10/2016 | Deshpande | A61F 2/586 |
| 2017/0266075 | A1* | 9/2017 | Becchi | A63B 23/16 |
| 2018/0055591 | A1* | 3/2018 | Bonny | A61B 90/57 |
| 2018/0228407 | A1* | 8/2018 | Olds | A61B 5/225 |
| 2019/0060099 | A1* | 2/2019 | Ciocarlic | A41D 19/00 |
| 2019/0204921 | A1* | 7/2019 | Goupil | G06F 3/016 |
| 2019/0209086 | A1* | 7/2019 | Huang | A61H 1/0288 |
| 2019/0380857 | A1* | 12/2019 | Gelanyi | B25J 9/1085 |
| 2019/0380865 | A1* | 12/2019 | Baschnagel | A61H 9/0092 |
| 2020/0046537 | A1* | 2/2020 | Plecnik | A61F 5/013 |
| 2020/0050269 | A1* | 2/2020 | Gu | B25J 9/0006 |
| 2020/0069504 | A1* | 3/2020 | Xue | B25J 9/0006 |
| 2021/0022899 | A1* | 1/2021 | Anunike | A61F 5/013 |
| 2021/0106489 | A1* | 4/2021 | Bhugra | A61H 1/0285 |
| 2021/0145687 | A1* | 5/2021 | Baldoni | A61H 1/0281 |
| 2021/0186792 | A1* | 6/2021 | Ewaldsson | A61B 5/6825 |
| 2021/0369535 | A1* | 12/2021 | Ishimine | A61H 1/0288 |
| 2022/0096309 | A1* | 3/2022 | Realmuto | A61H 1/0285 |
| 2022/0117823 | A1* | 4/2022 | Sobrepera | A61F 5/013 |
| 2022/0304888 | A1* | 9/2022 | Faii Ong | A61H 23/0254 |

OTHER PUBLICATIONS

"Curved Mirror," Wikipedia, retrieved from https://en.wikipedia.org/w/index.php?title=Curved_mirror&oldid=947730631, Mar. 28, 2020, seven pages.

"Instant Centre of Rotation," Wikipedia, retrieved from https://en.wikipedia.org/w/index.php?title=Instant_centre_of_rotation&oldid=917185535, Sep. 22, 2019, six pages.

Definition of "Pawl" by Merriam-Webster, retrieved from https://www.merriam-webster.com/dictionary/pawl, Apr. 12, 2021, eight pages.

* cited by examiner

UPPER BODY HUMAN TO MACHINE INTERFACE

CROSS-REFERENCE TO RELATED APPLICATION

This application claims priority to U.S. Provisional Patent Application No. 63/009,750 filed on Apr. 14, 2020 and entitled "Upper Body Human to Machine Interface", the content of which is hereby incorporated by reference.

STATEMENT AS TO RIGHTS TO INVENTIONS MADE UNDER FEDERALLY SPONSORED RESEARCH AND DEVELOPMENT

This invention was made with government support under Grant no. 1602085 and Grant no. 1747024 awarded by the National Science Foundation. The government has certain rights in the invention.

BACKGROUND

As addressed in U.S. Pat. No. 10,463,560, exoskeletons are mechatronic systems worn by a person in such a way that a direct transfer of mechanical power from the exoskeleton occurs. These robotic mechanisms have been applied in a variety of settings, for example, telemanipulation, man-amplification, rehabilitation, and to assist impaired human motor control. However, many of these applications of exoskeleton devices have yet to find widespread use, acceptance, or practicality.

One example area in which these devices have been proposed is the treatment of stroke. Stroke affects thousands of Americans every year and the recovery process is long, difficult, and costly. The use of a robotic exoskeleton may potentially reduce the length, difficulty, and cost of this recovery process. Various efforts have been proposed to provide a robotic exoskeleton for the upper-body.

BRIEF DESCRIPTION OF THE DRAWINGS

Features and advantages of embodiments of the present invention will become apparent from the appended claims, the following detailed description of one or more example embodiments, and the corresponding figures. Where considered appropriate, reference labels have been repeated among the figures to indicate corresponding or analogous elements.

FIG. 7 is configured for a right hand.

FIG. 13 is configured for a left hand.

DETAILED DESCRIPTION

Figure 1:
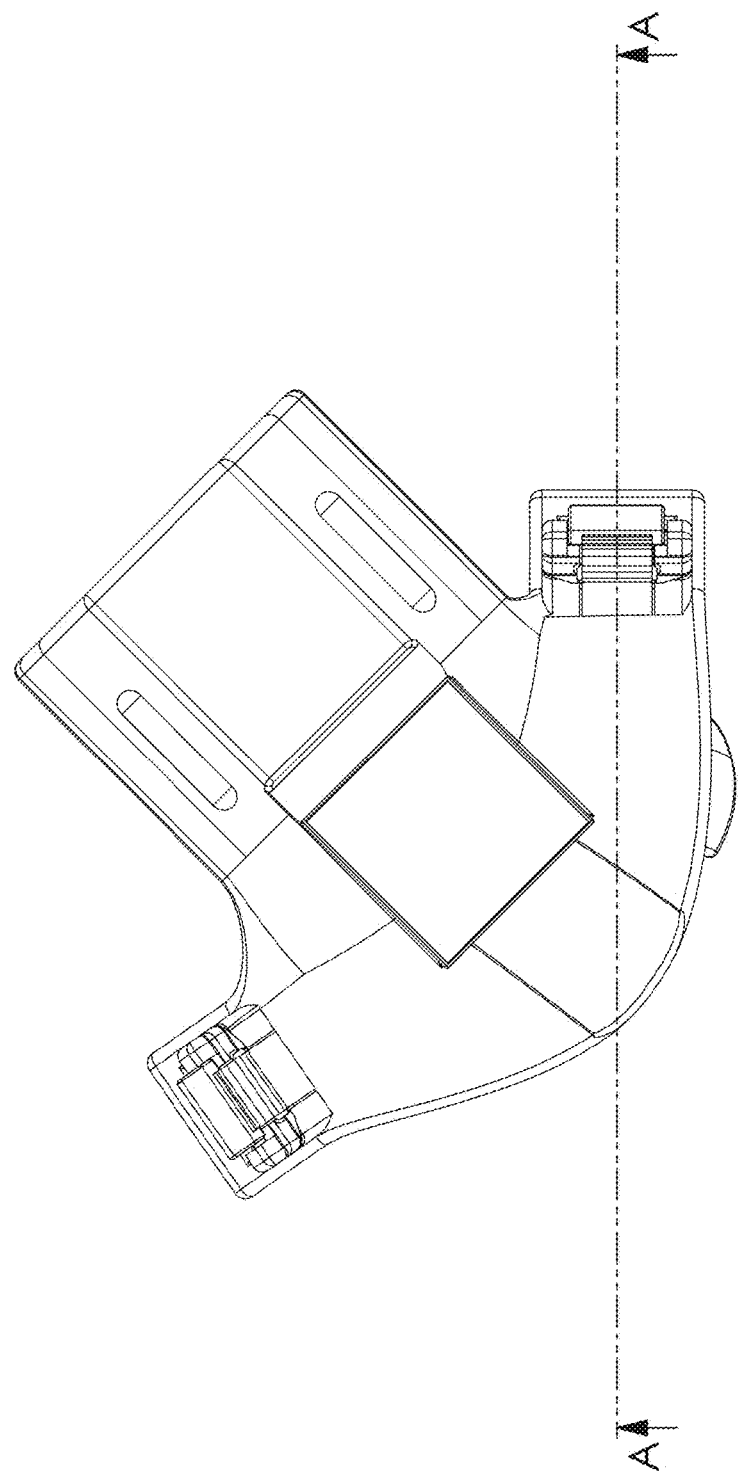
FIG. 1 includes a back view of an embodiment of the invention.

Reference will now be made to the drawings wherein like structures may be provided with like suffix reference designations. In order to show the structures of various embodiments more clearly, the drawings included herein are diagrammatic representations of structures. Thus, the actual appearance of the fabricated structures, for example in a photo, may appear different while still incorporating the claimed structures of the illustrated embodiments (e.g., walls may not be exactly orthogonal to one another in actual fabricated devices). Moreover, the drawings may only show the structures useful to understand the illustrated embodiments. Additional structures known in the art may not have been included to maintain the clarity of the drawings. For example, not every layer of a device is necessarily shown. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner. "Connected" may indicate elements are in direct physical or electrical contact with each other and "coupled" may indicate elements co-operate or interact with each other, but they may or may not be in direct physical or electrical contact. Phrases such as "comprising at least one of A or B" include situations with A, B, or A and B.

An embodiment includes an attachment method for connecting the hand to a wearable robot. An embodiment includes a Physical Human Robot Interaction (PHRI) interface of upper body wearable robots. An embodiment serves to couple the human hand to a mechanical device, primarily but not limited to a wearable robotic system with the following primary functions: (1) to anchor the human limb to the device and minimize the relative motion between the two, (2) transfer motion and force between the wearable device and the human, (3) to ensure user comfort during the duration of wearing the device, (4) to reduce adverse neuromuscular tendencies such as flexor synergy by the design to minimize contact and pressure on locations that are known to trigger them, (5) to assist the user or care giver in positioning and attaching the limb, especially for users with high muscle spasticity, and/or (6) to be resistant to loosening or slippage of the interface during the duration of use.

An embodiment relies at least in part on one or more of the following principles/characteristics/attributes: (1) ensuring broad and mildly compliant contact with the dorsal (back) surface of the hand for distribution of pressure, (2) ensuring that all (or most) palmar contact is directed to the regions of the Thenar and Hypothenar Eminences, which are known to be less provocative of flexor synergy, an adverse condition common in stroke affected patients that cause muscles to contract involuntarily, (3) a plastic-on-plastic ratcheting mechanism that allows caregivers to progressively move the hand into position while working on slowly reducing spasticity to allow extension, (4) grip across the metacarpal heads, dorsum and hypothenar eminence for functional therapy with medical robotic devices, and/or (5) a quick disconnect mechanism for attaching PHRI to the robot.

An embodiment has: (1) contact points of the Thenar and Hypothenar eminences, (2) a virtual center of rotation for the eminence contact surfaces, with one approximately centered about the axis of thumb flexion and the other approximately running along the gap between, for example, the 3rd and 4th metacarpal, (3) a plastic-on-plastic ratcheting mechanism to hold the position of the eminence contact points as they are tightened, and/or (4) a quick disconnect feature for quick wearable robot on/off without undoing the PHRI from the limb.

Conventional technology for PHIR largely relies on the use of handles or full contact along the palmar surface of the hand. In contrast, an embodiment ensures all (or most) palmar contact is directed to the regions of the Thenar and Hypothenar Eminences, which are known to be less provocative of flexor synergy than directing force along the palmar surface of the hand.

FIG. 1 includes a top view of a PHIR and section line in an embodiment.

Figure 2:
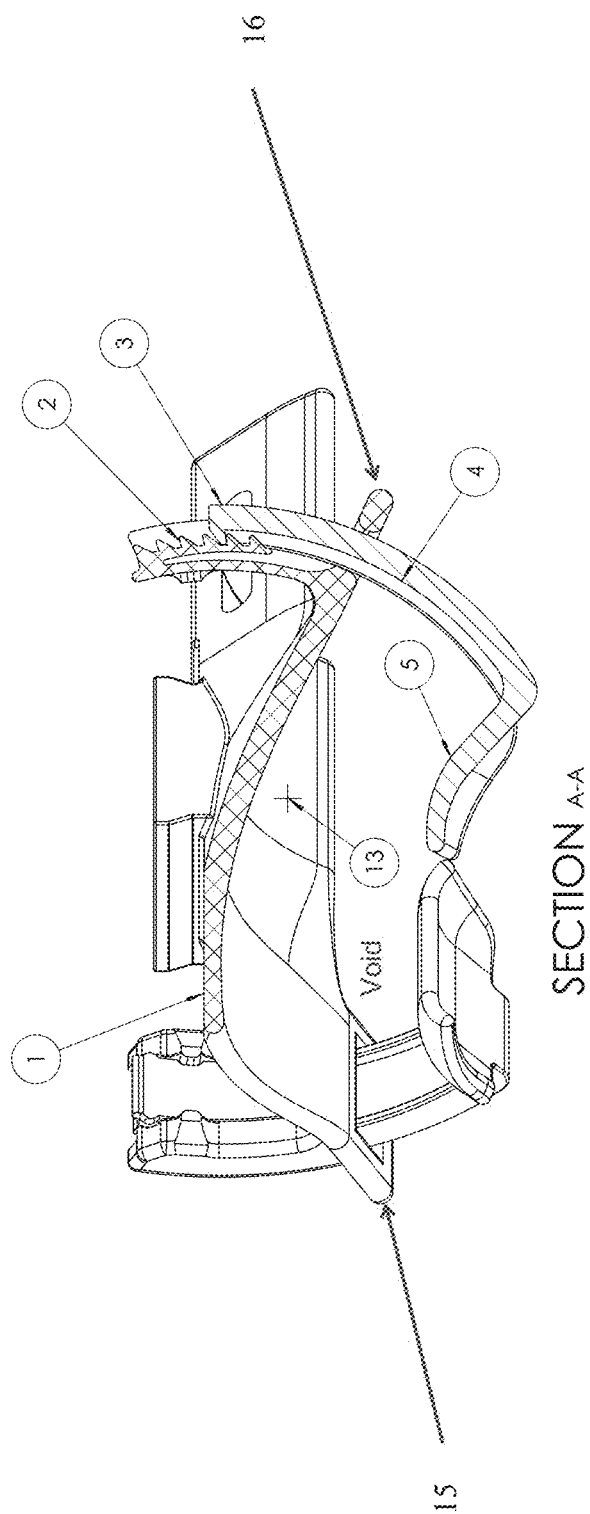
FIG. 2 includes a cross-sectional view of the embodiment of FIG. 1.

FIG. 2 includes a section view of a ratchet mechanism for the embodiment of FIG. 1. The hand support includes a rigid concave back of hand support (1), a curved ratchet feature on the back of hand support (2), a curved pawl (3), a radius with its center inside the hand allowing for rotation of a pawl component about center (4), an interface for applying pressure to thenar or hypothenar eminences (5), and a center of pawl rotation (13).

Figure 3:
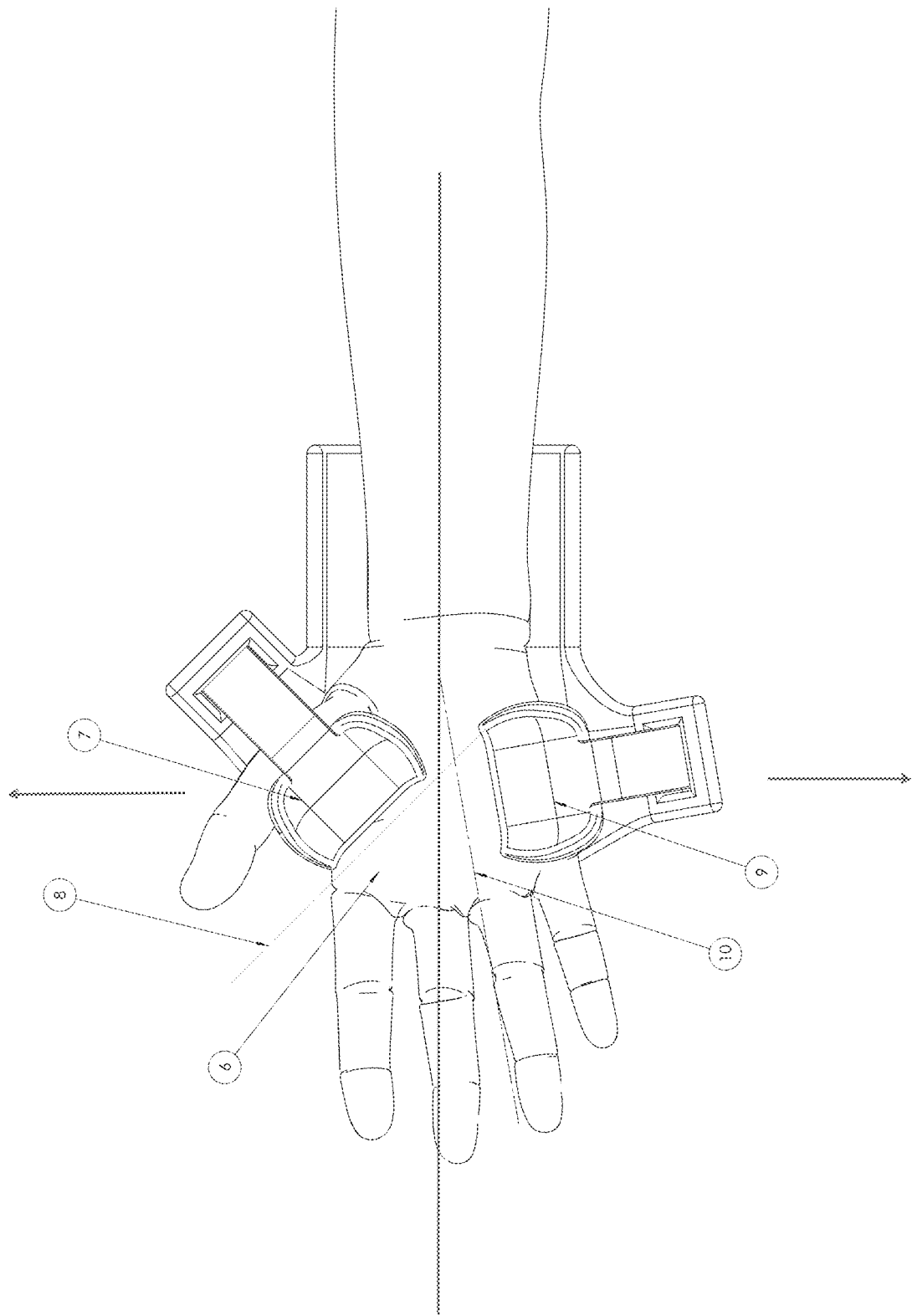
FIG. 3 includes a front view of the embodiment of FIG. 1.

FIG. 3 includes a hand (6), thenar pawl (7), thenar pawl axis of rotation (8), hypothenar pawl (9), and hypothenar pawl axis of rotation (10).

Figure 4:
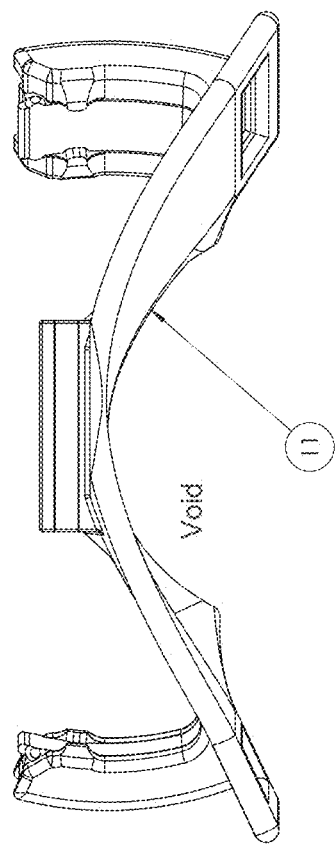
FIG. 4 includes a top view of the embodiment of FIG. 1.

FIG. 4 includes a concave surface (11) for back of hand support and locating the wrist.

Figure 5:
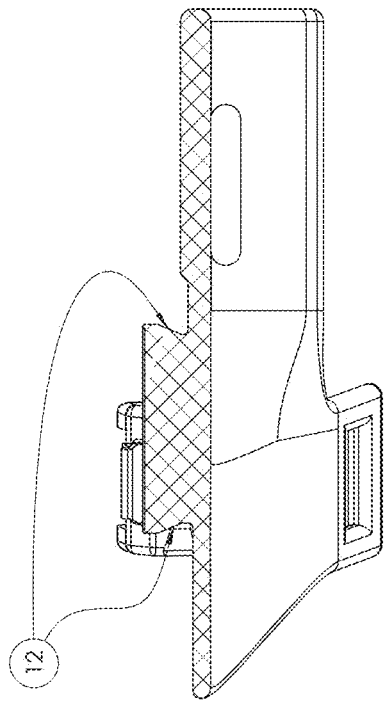
FIG. 5 includes a cross-sectional view of the embodiment of FIG. 1.

FIG. 5 includes male dovetail features (12) for a quick disconnect mechanism for attachment of the apparatus to a robot.

In an embodiment the ratchet systems include a one-way locking mechanism for contacting Thenar and Hypothenar eminences and a center of rotation inside the hand. However, in other embodiments the ratchet could instead include, for example, a cam mechanism or other one-way motion mechanism. A ratchet allows a therapist to assist patients with muscle spasticity to slowly and more comfortably spread the hand. A center of rotation (for the contact surfaces of the two pawls shown in FIG. 4) inside the hand provides a more comfortable tightening motion because the contact surface moves in the same arc as the eminences. An open hand position can be important to fight spasticity and flexor synergy, which are common post stroke conditions. Contact pressure on the center of the palm is known to sometimes trigger flexor synergy and contacting the thenar and hypothenar eminences helps avoid this. A concave rigid back of hand support includes mating features for a ratchet and includes a quick disconnect feature. Pressure from ratchets forces the back of hand into the curve of the rigid back of hand support. Contact between the rigid back of hand support and the back of the hand allows for the most direct interface between the PHRI and the bones of the palm, wrist, and forearm. As a result, good locating accuracy between the interface and the human body is achieved and unwanted freedom inside the PHRI is reduced. The quick disconnect feature allows for quickly taking the medical device on/off of the patient, freedom for a therapist to attach PHRI's outside to a robot, and reducing medical device downtime for patient switching.

An embodiment includes at least one of the following key features: (1) virtual center of rotation for the eminence contact surfaces, with one centered about the axis of thumb flexion and the other running along the gap between, for example, the 2nd and 3rd metacarpal (or between the $3^{rd}$ and $4^{th}$ metacarpals), (2) contact points of the Thenar and Hypothenar eminences, and/or (3) a plastic-on-plastic ratcheting mechanism to hold the position of the eminence contact points as they are tightened.

While embodiments are suitable for hand rehabilitation devices, other embodiments may be used in, more generally, man-machine interfaces and the like.

The embodiments of FIGS. 7 to 17 are now addressed.

An embodiment includes an apparatus comprising primary platform 17, which is configured to support a hand and a forearm. Secondary platform 18 is statically coupled to the primary platform. For example, see coupler 19, which statically couples the second platform to the primary platform. Such a coupler may include a screw, bolt, rod, staple, tie-wrap, wire, string, mortise/tenon, dovetail joint, and the like. Primary strap 21 is coupled to the primary platform. The primary strap is configured to secure the forearm to the primary platform. Secondary strap 20 is coupled to the secondary platform. The secondary strap is configured to secure the hand to the secondary platform. Coupler 22 couples the primary platform to a robot 23.

The primary platform includes a central long axis 24 and the secondary platform includes a central long axis 25. The central long axis of the secondary platform is not parallel to the central long axis of the primary platform, and the central long axis of the secondary platform is not orthogonal to the central long axis of the primary platform. An additional axis 26 is orthogonal to the central long axis of the primary platform, and the additional axis intersects both of the primary and second platforms as well as a void 27 that exists between portions of the primary and second platforms.

The second platform has first and second ends 28, 29 that oppose each other and which both intersect the central long axis 25 of the secondary platform. The second end only couples to the primary platform via the first end, and the void 27 exists between the second end and the primary platform.

Figure 11:
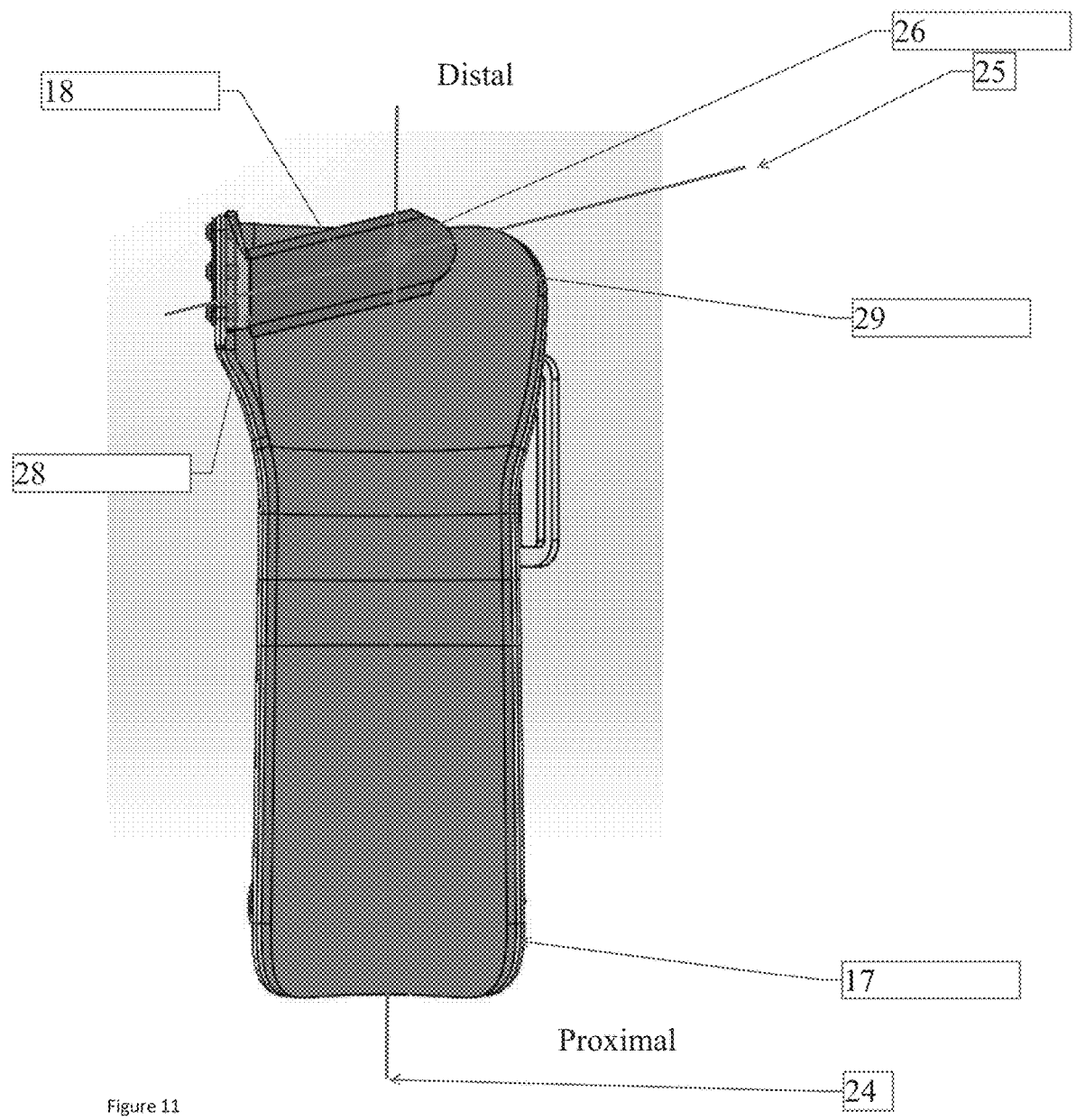
FIG. 11 includes a front view of the embodiment of FIG. 7.
Figure 12:
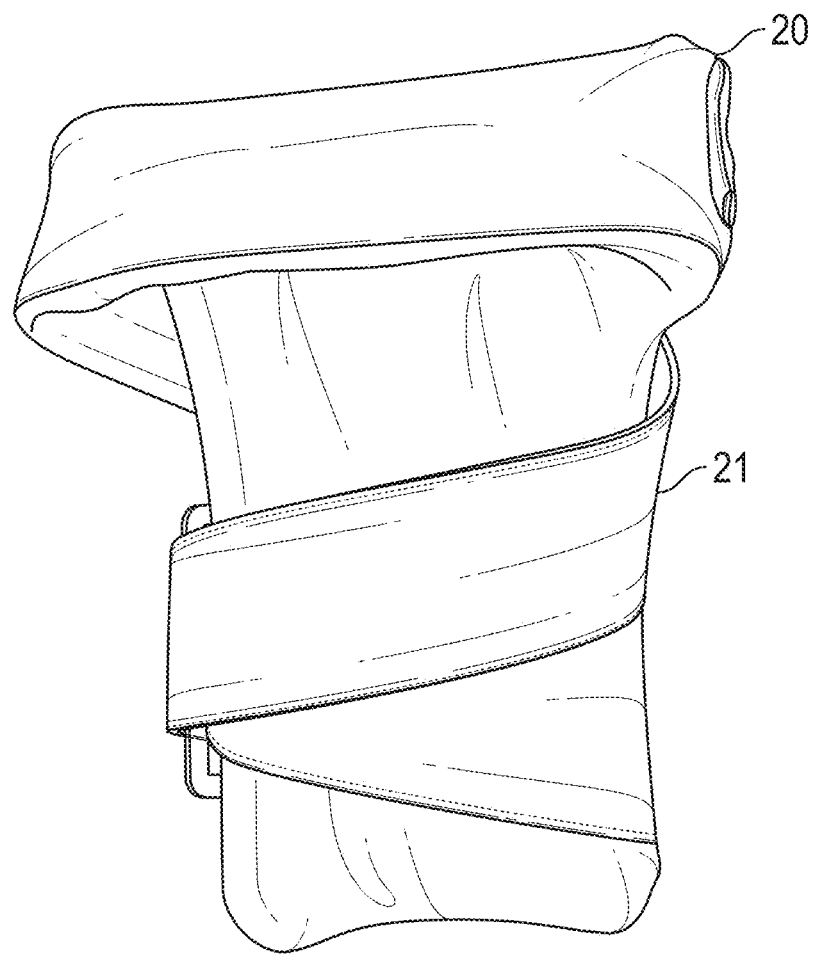
FIG. 12 includes a front view of an embodiment of the invention.
Figure 13:
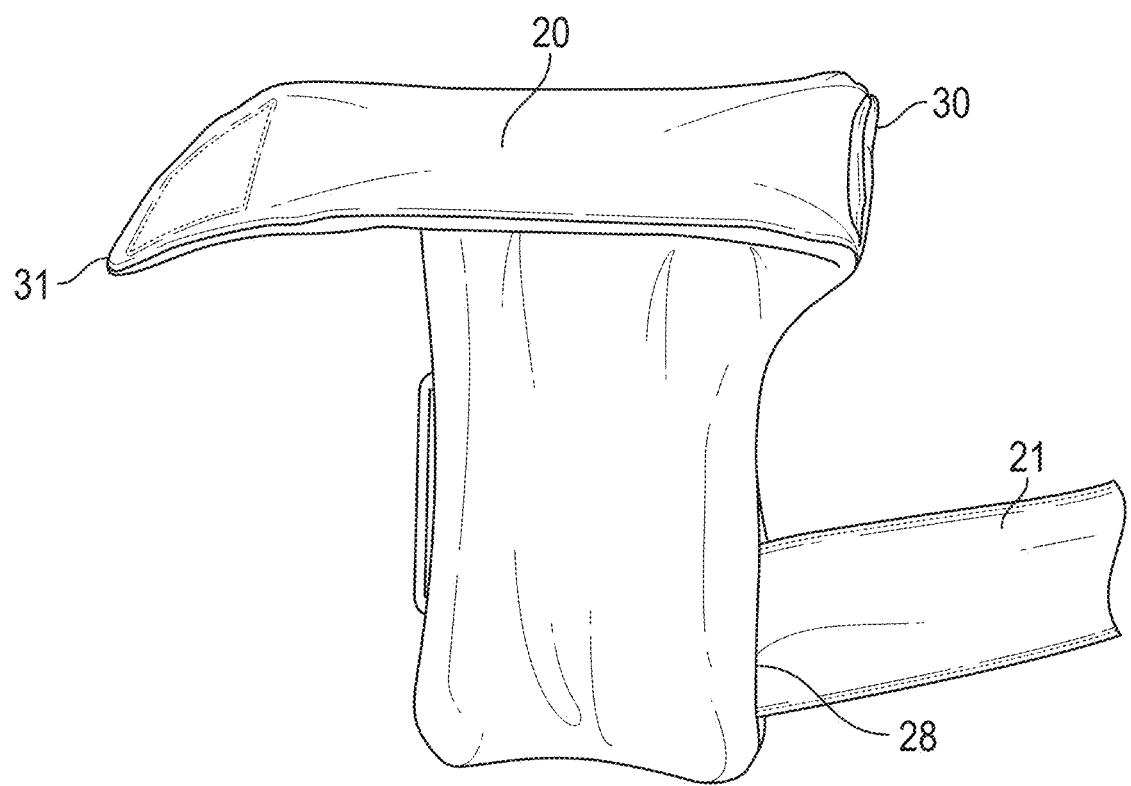
FIG. 13 includes a front view of the embodiment of FIG. 12.
Figure 14:
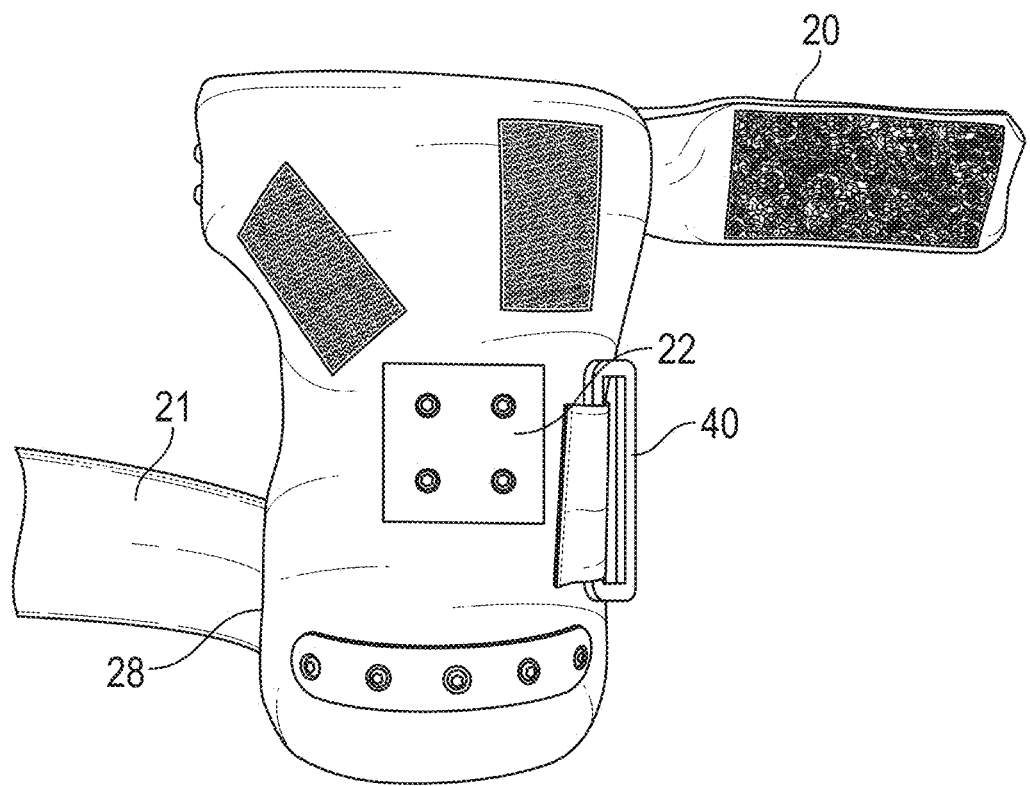
FIG. 14 includes a back view of the embodiment of FIG. 12.
Figure 15:
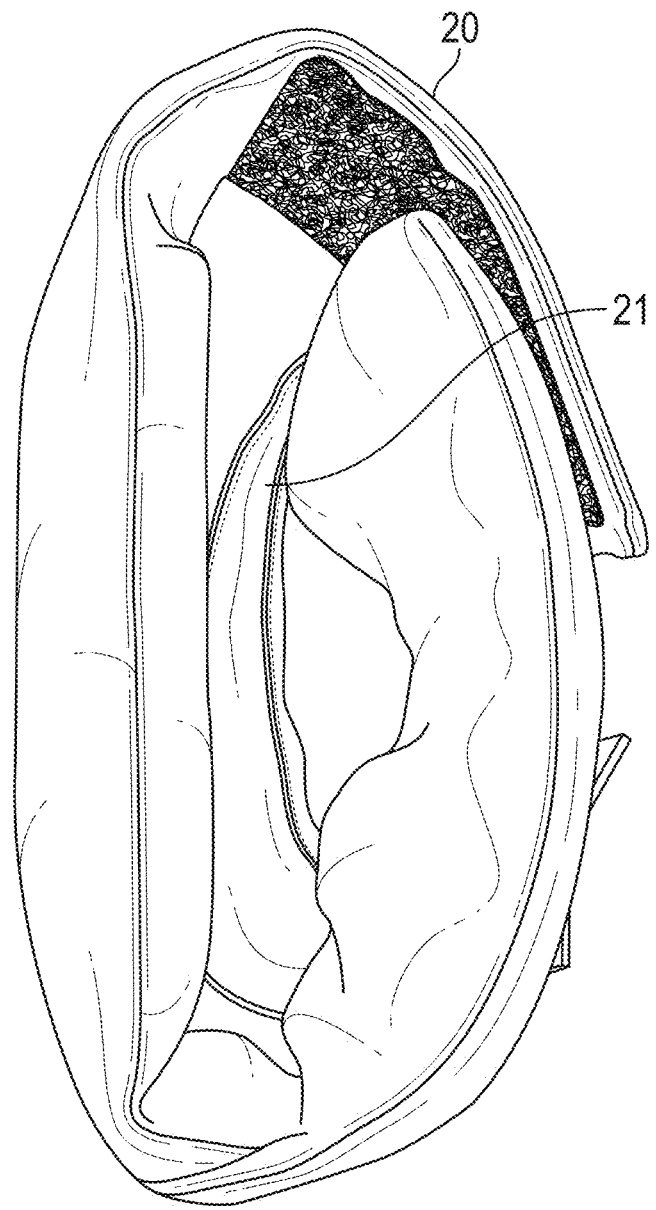
FIG. 15 includes a top view of the embodiment of FIG. 12.
Figure 16:
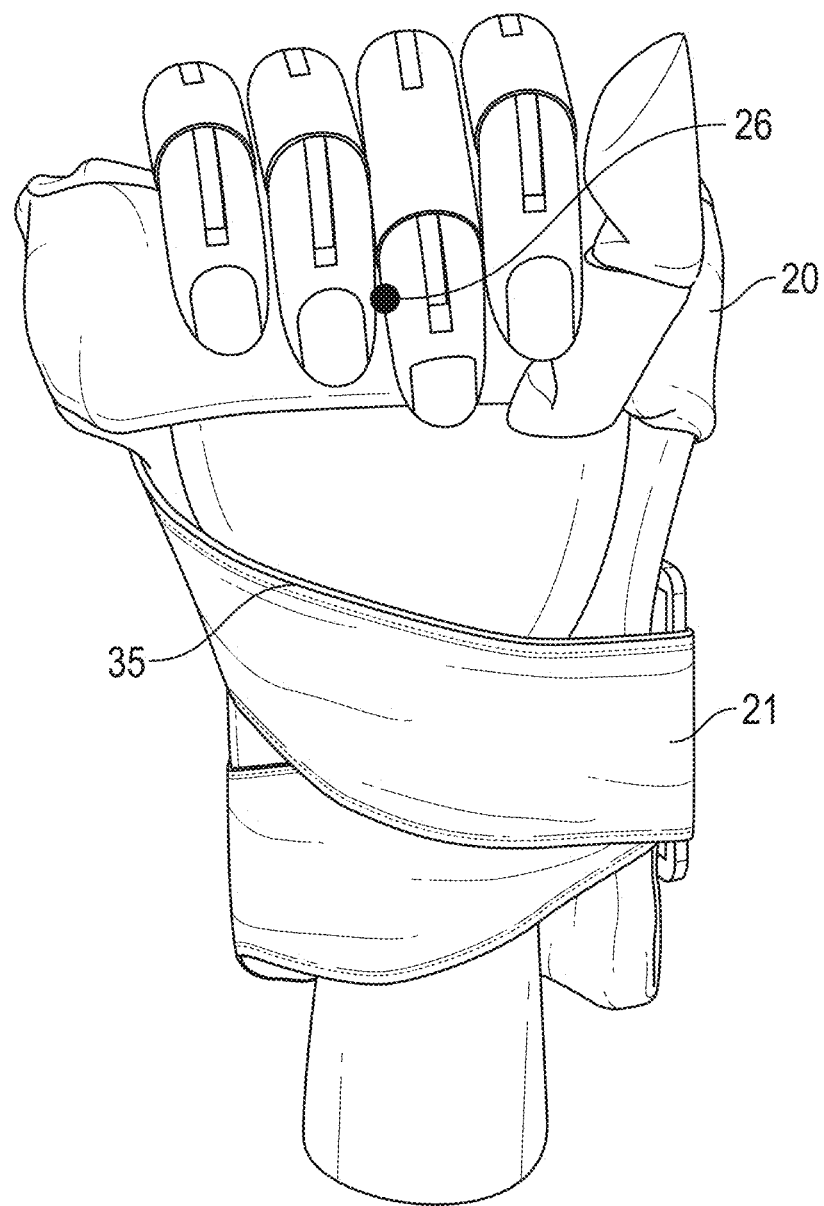
FIG. 16 includes a front view of the embodiment of FIG. 12.
Figure 17:
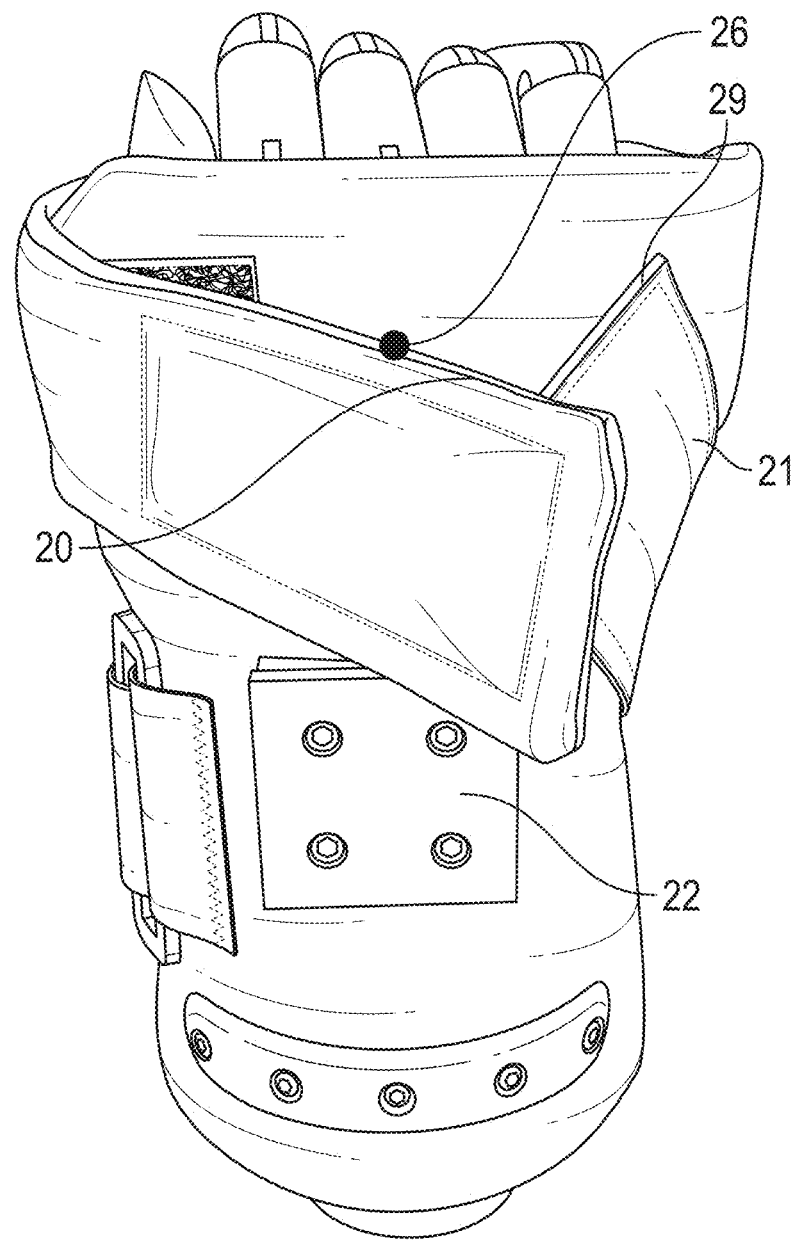
FIG. 17 includes a back view of the embodiment of FIG. 12.
Figure 18:
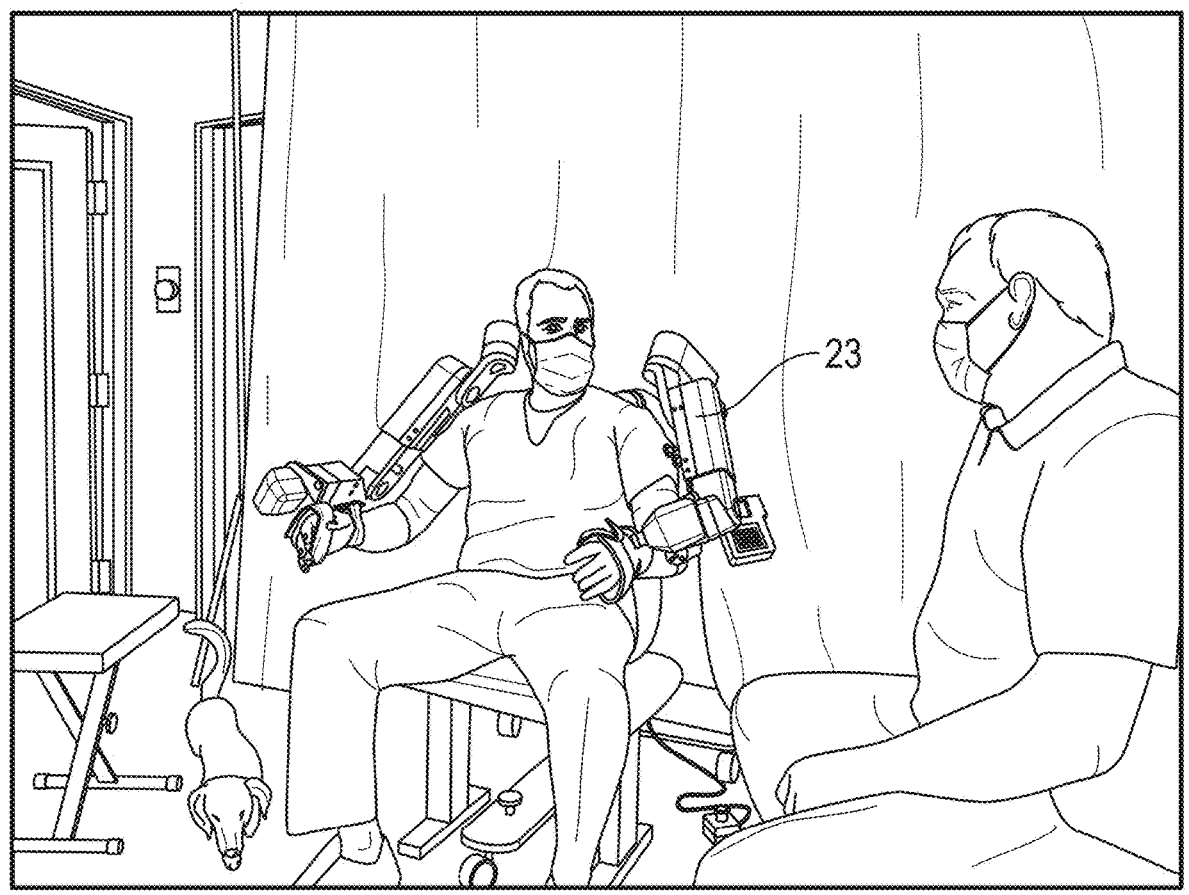
FIG. 18 includes a perspective view of an embodiment of the invention.
Figure 19:
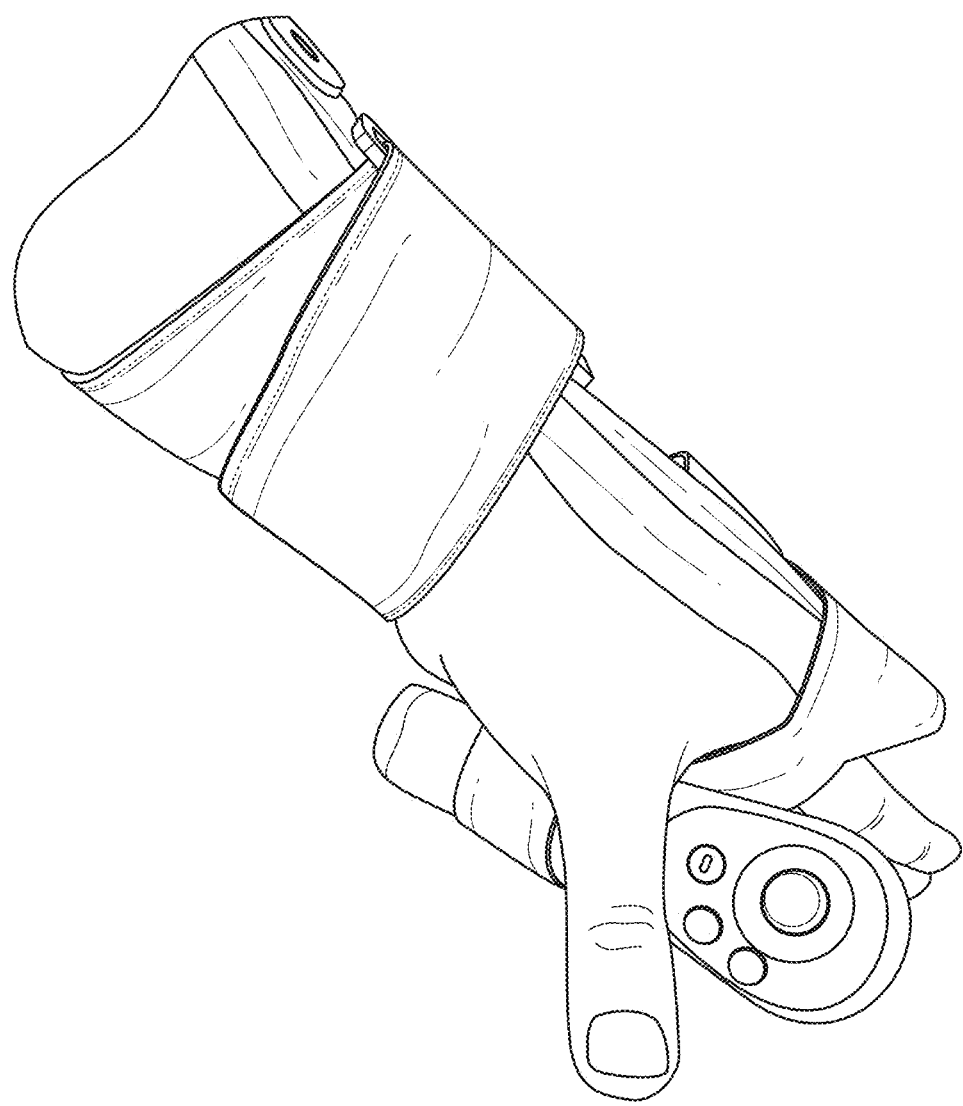
FIG. 19 includes a perspective view of an embodiment of the invention.

As seen in FIG. 11, the second end of the second platform is distal to the first end of the second platform. The central long axis of the second platform ("second" and "secondary" are at times used interchangeably herein) extends distally as the central long axis of the secondary platform extends from the first end of the second platform to the second end of the second platform. In other words, as the secondary platform moves left to right in FIG. 11 the platform slopes distally or upwards. This helps align the secondary platform to the metacarpal heads, which can avoid pressure in the palm and associated undesirable muscle contractions. Put another way, as shown in FIG. 12, the secondary strap is distal to the primary strap; and the second end of the second platform (FIG. 11) is distal to the first end of the second platform.

The primary strap 21 has first and second ends 28, 29 that oppose each other. The first end 28 of the primary strap is fixed to the primary platform. The second strap has first and second ends 30, 31 which oppose each other. The first end of the secondary strap is fixed to the secondary platform. For example, in FIG. 13 the second strap (visible) is placed over the second platform (not visible).

In a first configuration (FIGS. 13 and 14): (a) the second end of the primary strap is only secured to the primary platform indirectly via the first end of the primary strap; and (b) the second end of the secondary strap is only secured to the primary platform indirectly via the first end of the second strap.

In a second configuration (FIGS. 12, 15, 16, 17): (a) the second end of the primary strap is secured directly to the primary platform and is configured to secure the forearm to the primary platform; and (b) the second end of the secondary strap is secured directly to the primary platform via the first end of the second strap and is configured to secure the hand to the primary platform. The second configuration is configured to secure the forearm and the hand to the primary platform such that the additional axis 26 intersects both of the primary and second platforms and metacarpals of the hand.

The primary platform includes first and second lateralmost opposing edges 32, 33 that are coupled to each other by a curved wall 34 of the primary platform. The curved wall includes a midpoint that is equidistant from the first and second lateral-most opposing edges. The first lateral-most edge, the second lateral-most edge, and the curved wall collectively form void 27 that is configured to receive the hand. Void 27 and coupler 22 are on opposite sides of the curved wall.

In the second configuration second end 29 of the primary strap is distal to the primary end of the primary strap. As a result, the primary strap is configured to directly contact a hypothenar eminence 35 of the hand.

First end 28 of the secondary platform is fixed to the primary platform via at least one coupler 19. The secondary platform is configured to be decoupled from the primary platform by decoupling the at least one coupler from the primary platform. For instance, see FIG. 20 where no coupler is visible at location 36 and the secondary platform is not installed.

Figure 20:
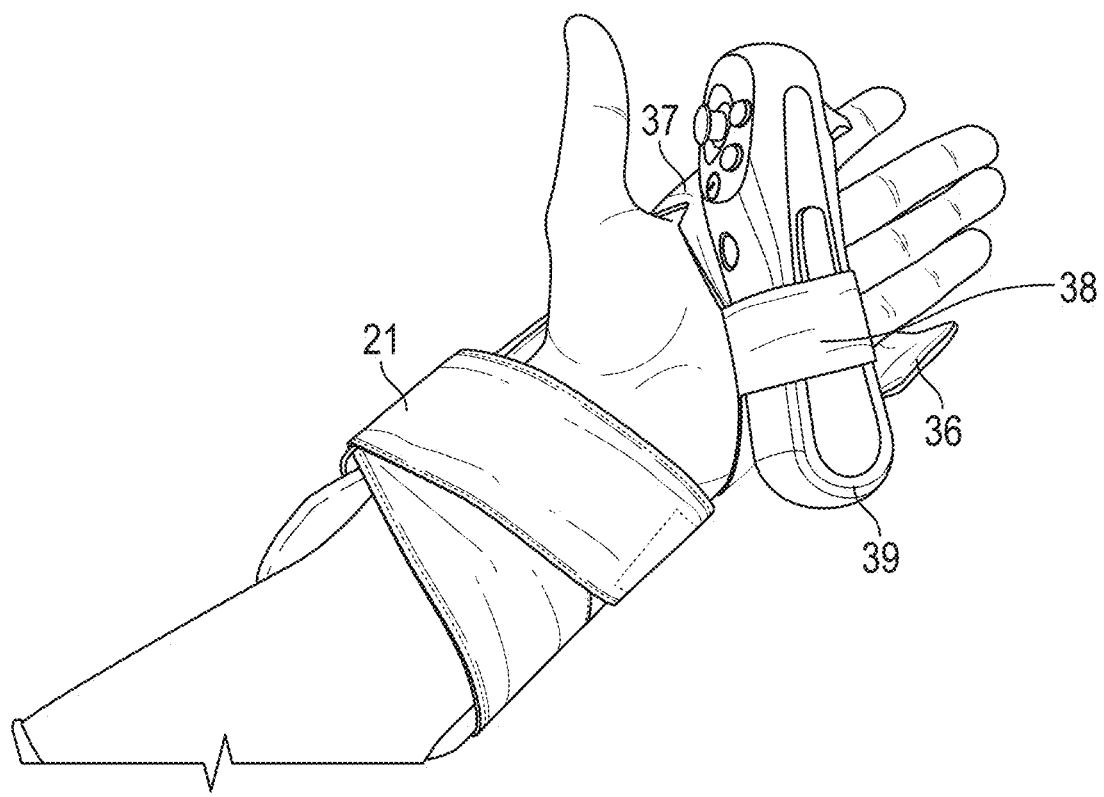
FIG. 20 includes a front view of the embodiment of FIG. 12.

In FIG. 20 tertiary strap 37 is configured to affix to the primary platform distal to the primary strap 21. The tertiary strap includes coupler 38 to couple sensor 39 to the primary platform. For example, a simple loop is a coupler that couples a sensor (e.g., virtual reality controller) to strap 37. Couplers may include straps, hook and loop fasteners, strings, wires, and the like.

Similar to FIG. 20, in another embodiment the secondary strap (instead of the tertiary strap of FIG. 20) includes a coupler to couple a sensor to the primary platform.

Various examples of embodiments are now addressed.

Example 1. An apparatus comprising: a thenar eminence restraint that includes at least one ratchet tooth; a hypothenar eminence restraint that includes at least one ratchet tooth; a hand support that includes: (a) at least one ratchet tooth to mate with the at least one ratchet tooth of the thenar eminence restraint to form a first ratchet, and (b) at least one additional ratchet tooth to mate with the at least one ratchet tooth of the hypothenar eminence restraint to form a second ratchet; wherein the hand support includes first and second lateral-most opposing edges that are coupled to each other by a curved wall, the curved wall including a midpoint that is equidistant from the first and second lateral-most opposing edges; wherein the first lateral-most edge, the second lateral-most edge, and the curved wall collectively form a void to receive a patient's hand; wherein the first ratchet has an axis of rotation included within the void and the second ratchet has an axis of rotation included within the void.

While the embodiment of Example 1 uses a ratchet, other embodiments may use various forms of uni-directional locking devices. For example, an embodiment may include a cam or strap. Such a strap may be extended along a curved surface and still have an axis of rotation that is not included in a patient's hand. Other locking mechanisms and/or couplers may include hook and loop fasteners, treasure locks, friction locks, and the like.

Also, the curved wall does not necessarily mean the wall has a center of curvature or that the wall has a constant arc. Other embodiments may have walls that are not curved while still providing a void.

Another version of Example 1: An apparatus comprising: a thenar eminence restraint that includes at least one ratchet tooth; a hypothenar eminence restraint that includes at least one ratchet tooth; a hand support that includes: (a) at least one ratchet tooth to mate with the at least one ratchet tooth of the thenar eminence restraint to form a first ratchet, and (b) at least one additional ratchet tooth to mate with the at least one ratchet tooth of the hypothenar eminence restraint to form a second ratchet; wherein the hand support includes first and second lateral-most opposing edges that are coupled to each other by a curved wall; wherein the first lateral-most edge, the second lateral-most edge, and the curved wall collectively form a void to receive a patient's hand; wherein the first ratchet has an axis of rotation included within the void and the second ratchet has an axis of rotation included within the void.

Another version of Example 1: An apparatus comprising: a thenar eminence restraint that includes at least one ratchet tooth; a hypothenar eminence restraint that includes at least one ratchet tooth; a hand support that includes: (a) at least one ratchet tooth to mate with the at least one ratchet tooth of the thenar eminence restraint to form a first ratchet, and (b) at least one additional ratchet tooth to mate with the at least one ratchet tooth of the hypothenar eminence restraint to form a second ratchet; wherein the hand support includes first and second lateral-most opposing edges that are coupled to each other by a wall; wherein the first lateral-most edge, the second lateral-most edge, and the wall collectively form a void to receive a patient's hand; wherein the first ratchet has an axis of rotation included within the void and the second ratchet has an axis of rotation included within the void.

Thus, the wall need not be curved or have any one particular shape.

Example 2. The apparatus of Example 1 wherein the first ratchet is curved and the second ratchet is curved.

Example 3. The apparatus according to any of Examples 1-2 wherein the at least one ratchet tooth of the thenar eminence restraint includes a first pawl and the at least one ratchet tooth of the hypothenar eminence restraint includes a second pawl.

Thus, a ratchet tooth as used herein is construed broadly to include, for example, a pawl. A pawl, as used herein, may include a bar (e.g., a curved bar) or lever whose free end engages with the teeth of a cogwheel or ratchet so that the wheel or ratchet can only turn or move one way. Such a pawl may include a pivoted tongue or sliding bolt (or member) on one part of a machine that is adapted to fall into notches or interdental spaces on another part of a machine so as to permit motion in only one direction. The pawl need not be biased by any means (e.g., using a spring or natural resiliency of material used to make the pawl).

Example 4. The apparatus according to any of Examples 1-3 wherein: the thenar eminence restraint is configured to move towards the hand support as the first ratchet tightens; the hypothenar eminence restraint is configured to move towards the hand support as the second ratchet tightens.

Example 5. The apparatus of Example 4 wherein: in response to tightening the first ratchet, the thenar eminence restraint includes a surface to drive the thenar eminence laterally towards the first lateral-most edge and away from the midpoint of the curved wall; in response to tightening the second ratchet, the hypothenar eminence restraint includes a surface to drive the hypothenar eminence laterally towards the second lateral-most edge and away from the midpoint of the curved wall.

For example, in FIG. 2 the leader from element 5 points directly at a surface used to drive an anatomical feature, such as a prominence of the hand. FIG. 3 shows two arrows showing the lateral forces exerted on the hand. In an embodiment, the lateral forces include at least a component of force that is orthogonal to the long axis of the device, which is shown in FIG. 3. The lateral-most edges are shown in FIG. 2 with arrows 15, 16.

Example 7. The apparatus of Example 4 wherein: in response to tightening the first ratchet, the thenar eminence restraint includes a surface to drive the thenar eminence laterally towards the first lateral-most edge; in response to tightening the second ratchet, the hypothenar eminence restraint includes a surface to drive the hypothenar eminence laterally towards the second lateral-most edge.

Example 8. The apparatus according to any of Examples 1-7 comprising a coupler configured to couple the apparatus to a robot.

Example 9. The apparatus according to any of Examples 1-8 wherein the axis of rotation of the first ratchet is non-parallel to the axis of rotation of the second ratchet.

Example 10. A method comprising: coupling a patient's hand to a hand support, the hand support including: (a) at least one ratchet tooth to mate with at least one ratchet tooth of a thenar eminence restraint to form a first ratchet, (b) at least one additional ratchet tooth to mate with at least one ratchet tooth of a hypothenar eminence restraint to form a second ratchet; (c) first and second lateral-most opposing edges that are coupled to each other by a curved wall, the curved wall including a midpoint that is equidistant from the first and second lateral-most opposing edges; advancing the thenar eminence restraint towards the hand support to tighten the first ratchet and secure the thenar eminence to the hand support; advancing the hypothenar eminence restraint towards the hand support to tighten the second ratchet and secure the hypothenar eminence to the hand support; after coupling the patient's hand to the hand support, coupling the hand support to a robot.

Another version of Example 10: A method comprising: coupling a patient's hand to a hand support and first and second anatomical restraints; advancing the first anatomical restraint towards the hand support to secure a first portion of the hand to the hand support; advancing the second anatomical restraint towards the hand support to secure a second portion of the hand to the hand support; after coupling the patient's hand to the hand support, coupling the hand support to a robot.

Thus, not all methods are reliant upon the use of ratchets. Other embodiments may use other fasteners such as hook and loop systems.

Example 11. The method of Example 10, wherein the first lateral-most edge, the second lateral-most edge, and the curved wall collectively form a void to receive a patient's hand.

Example 12. The method of Example 11 comprising advancing the thenar eminence restraint towards the hand support to tighten the first ratchet by advancing the first ratchet along a curvilinear path and about an axis of rotation that is included within the void.

While in some embodiments the curvilinear path may include a portion of a circular path with a constant axis of rotation, in other embodiments the path may be elliptical and the like and may instead have an axis of rotation that changes over time depending on rotation of the restraint. In such a case the instantaneous axis of rotation is included within the void. An instantaneous axis of rotation (also called an instant center of rotation, instantaneous velocity center, or instantaneous center or instant center) is the point fixed to a body undergoing planar movement that has zero velocity at a particular instant of time. At this instant, the velocity vectors of the trajectories of other points in the body generate a circular field around this point which is identical to what is generated by a pure rotation.

Example 13. The method of Example 12 comprising advancing the hypothenar eminence restraint towards the hand support to tighten the second ratchet by advancing the second ratchet along an additional curvilinear path and about an additional axis of rotation that is included within the void.

Example 14. The method according to any of Examples 10-13 wherein the at least one ratchet tooth of the thenar eminence restraint includes a first pawl and the at least one ratchet tooth of the hypothenar eminence restraint includes a second pawl.

Example 15. The method according to any of Examples 10-14 comprising: advancing the thenar eminence restraint towards the hand support to tighten the first ratchet and drive the thenar eminence laterally towards the first lateral-most edge and away from midpoint of the curved wall; advancing the hypothenar eminence restraint towards the hand support to tighten the second ratchet and drive the hypothenar eminence laterally towards the second lateral-most edge and away from midpoint of the curved wall.

Example 16. The method according to any of Examples 10-14 comprising: advancing the thenar eminence restraint towards the hand support to tighten the first ratchet and drive the thenar eminence laterally towards the first lateral-most edge; advancing the hypothenar eminence restraint towards the hand support to tighten the second ratchet and drive the hypothenar eminence laterally towards the second lateral-most edge.

Example 17. The apparatus according to any of Examples 10-16 wherein the axis of rotation of the first ratchet is non-parallel to the additional axis of rotation of the second ratchet.

Example 18. An apparatus comprising: a first restraint that includes at least one ratchet tooth; a second restraint that includes at least one ratchet tooth; an anatomical support that includes: (a) at least one ratchet tooth to mate with the at least one ratchet tooth of the first restraint to form a first ratchet, and (b) at least one additional ratchet tooth to mate with the at least one ratchet tooth of the second restraint to form a second ratchet; wherein the anatomical support includes first and second lateral-most opposing edges that are coupled to each other by a wall; wherein the first lateral-most edge, the second lateral-most edge, and the wall collectively form a void to receive an anatomical feature; wherein the first ratchet has an axis of rotation included within the void and the second ratchet has an axis of rotation included within the void.

Example 19. The apparatus of Example 18 wherein the first ratchet is curved and the second ratchet is curved.

Example 20. The apparatus according to any of Examples 18-19 wherein the at least one ratchet tooth of the first restraint includes a first pawl and the at least one ratchet tooth of the second restraint includes a second pawl.

Example 21. The apparatus according to any of Examples 18-20 wherein: the first restraint is configured to move towards the anatomical support as the first ratchet tightens; the second restraint is configured to move towards the anatomical support as the second ratchet tightens.

Example 22. The apparatus of Example 21 wherein: in response to tightening the first ratchet, the first restraint includes a surface to drive a portion of the anatomical feature laterally towards the first lateral-most edge and away from a midpoint of the wall; in response to tightening the second ratchet, the second restraint includes a surface to drive another portion of the anatomical feature laterally towards the second lateral-most edge and away from midpoint of the wall.

Example 23. The apparatus of Example 21 wherein: in response to tightening the first ratchet, the first restraint includes a surface to drive a portion of the anatomical feature laterally towards the first lateral-most edge and away from a midpoint of the wall; in response to tightening the second ratchet, the second restraint includes a surface to drive another portion of the anatomical feature laterally towards the second lateral-most edge and away from the midpoint of the wall.

Example 24. The apparatus of Example 21 wherein: in response to tightening the first ratchet, the first restraint includes a surface to drive a portion of the anatomical feature laterally towards the first lateral-most edge; in response to tightening the second ratchet, the second restraint includes a surface to drive another portion of the anatomical feature laterally towards the second lateral-most edge.

Example 25. The apparatus according to any of Examples 18-24 comprising a coupler configured to couple the apparatus to a robot.

Example 26. The apparatus according to any of Examples 18-25 wherein the axis of rotation of the first ratchet is non-parallel to the axis of rotation of the second ratchet.

Example 27. An apparatus comprising: an anatomical restraint that includes at least one ratchet tooth; an anatomical support that includes at least one ratchet tooth to mate with the at least one ratchet tooth of the anatomical restraint to form a first ratchet; wherein the anatomical support includes first and second lateral-most opposing edges that are coupled to each other by a curved wall, the curved wall including a midpoint that is equidistant from the first and second lateral-most opposing edges; wherein the first lateral-most edge, the second lateral-most edge, and the curved wall collectively form a void to receive a patient's anatomical feature; wherein the first ratchet has an axis of rotation included within the void.

Thus, while most embodiments concern a hand, other embodiments may address other anatomical areas such as a foot instead of a hand.

Figure 6:
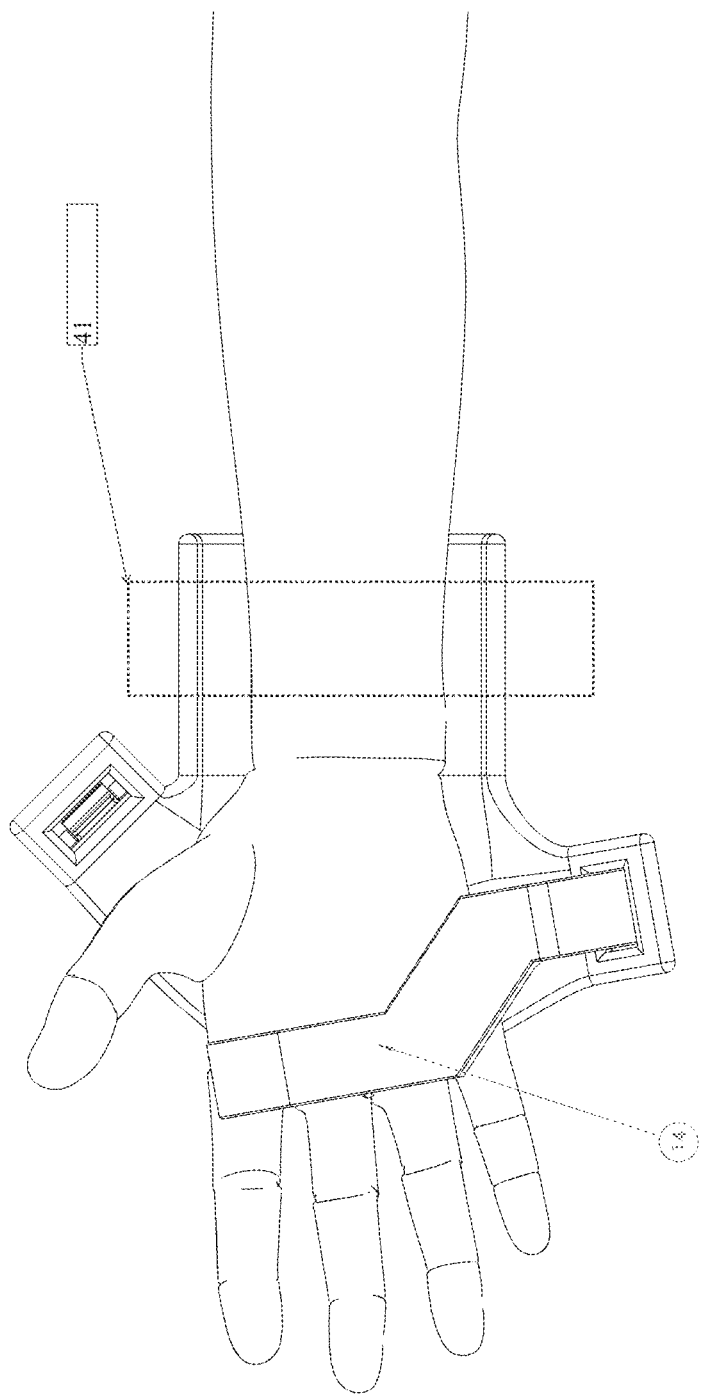
FIG. 6 includes a front view of an embodiment of the invention.
Figure 7:
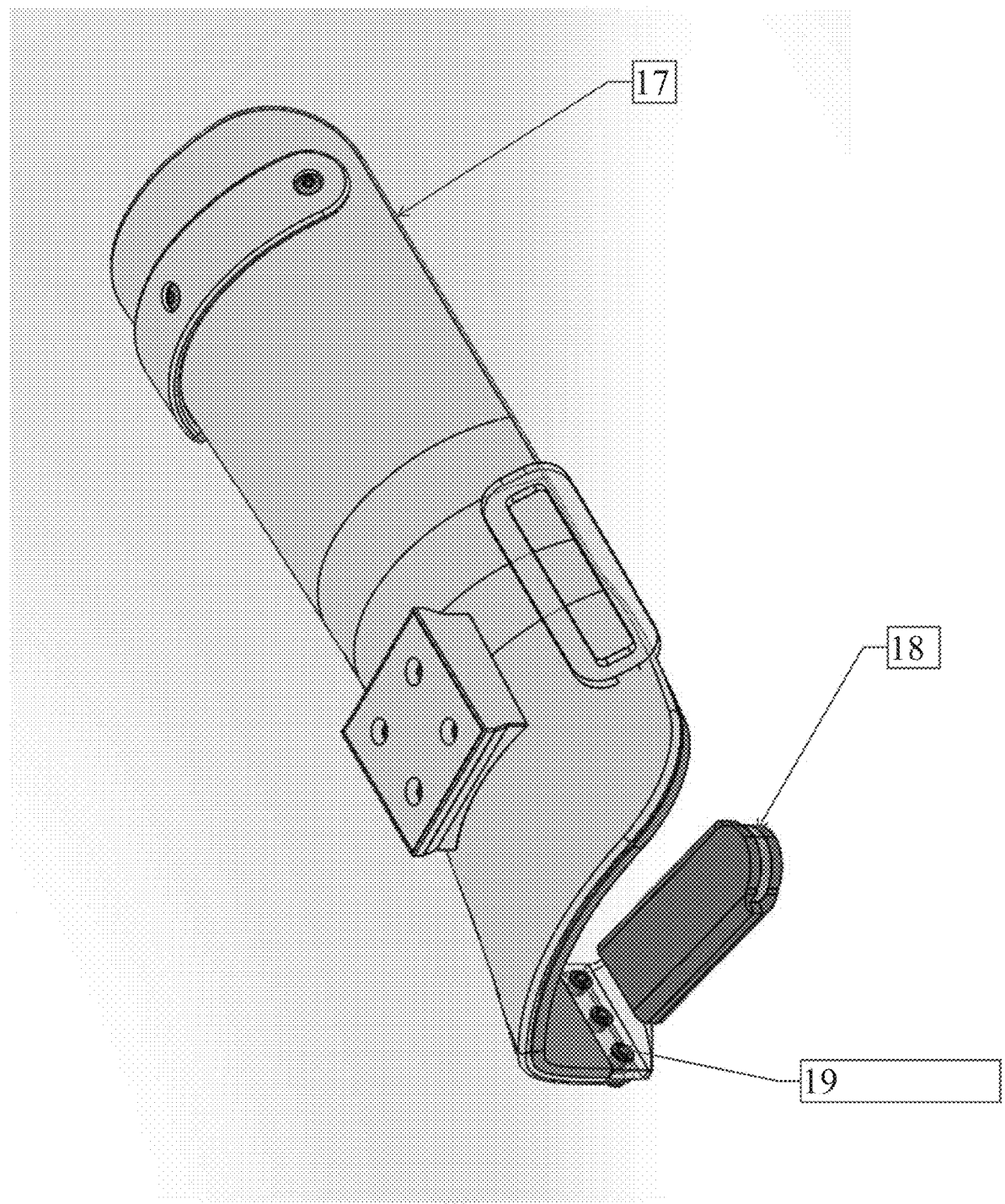
FIG. 7 includes a perspective view of an embodiment of the invention.
Figure 8:
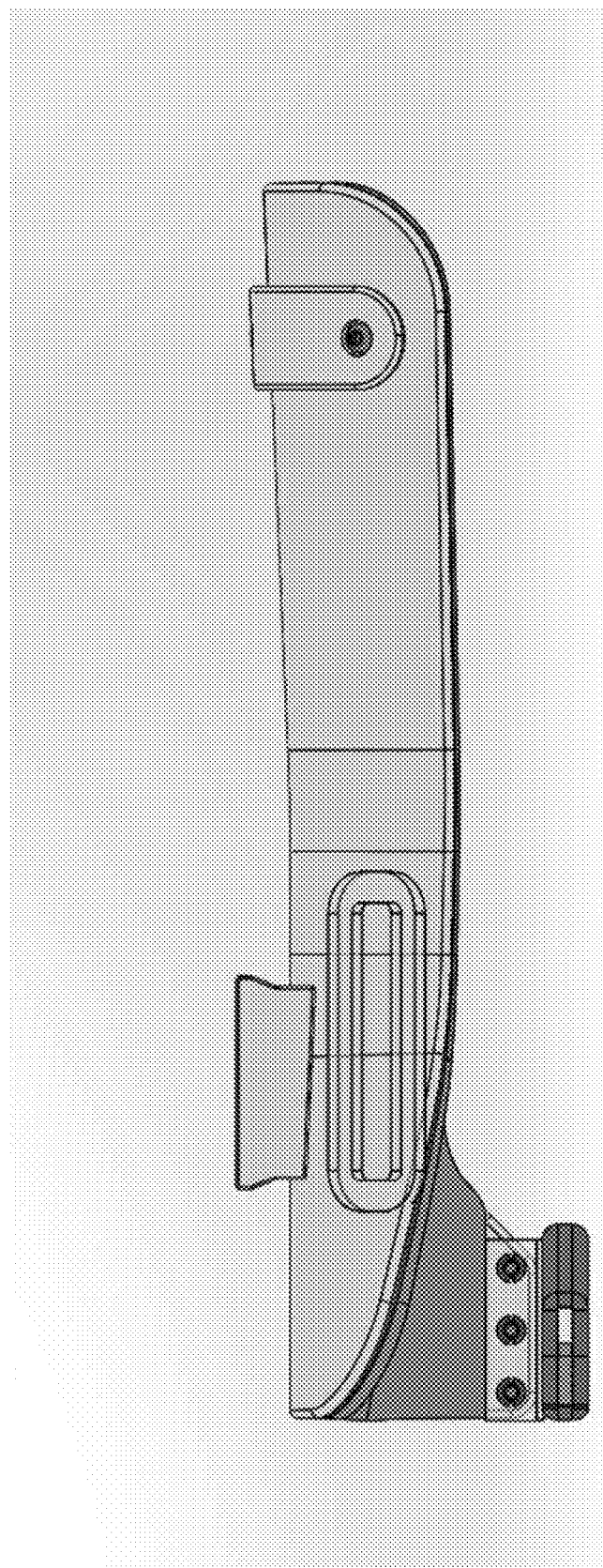
FIG. 8 includes a side view of the embodiment of FIG. 7.
Figure 9:
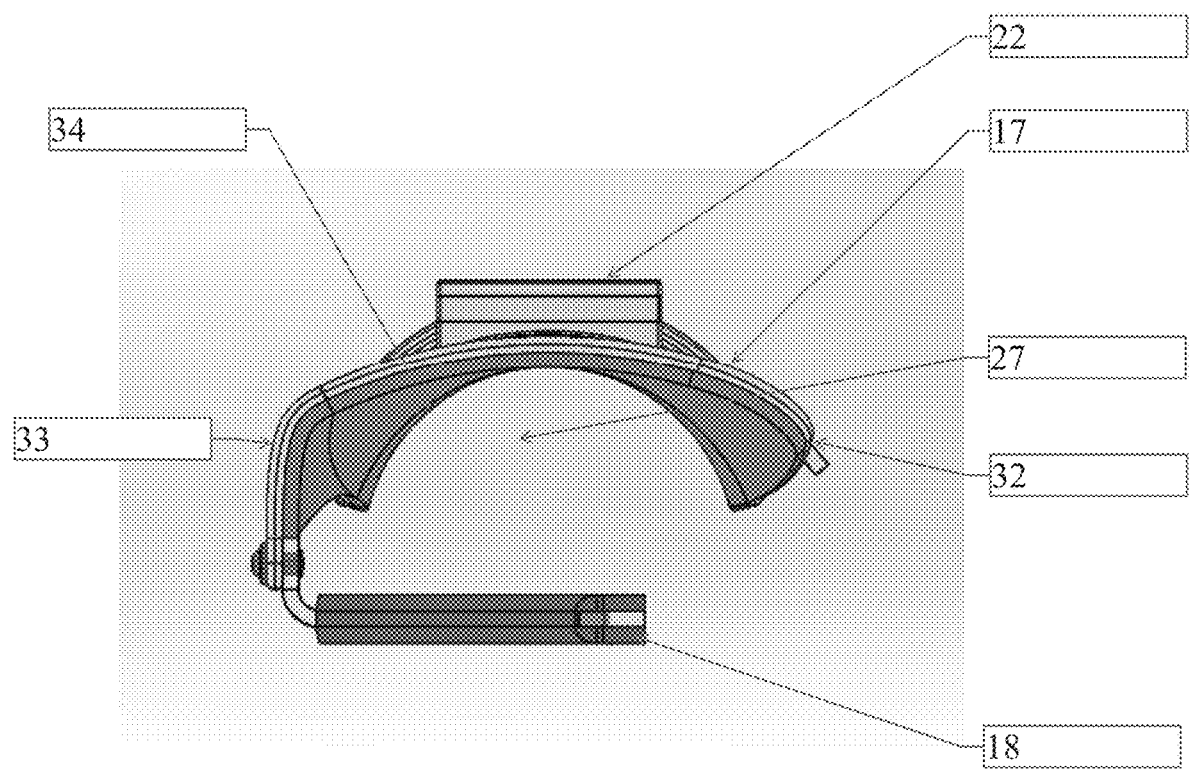
FIG. 9 includes a top view of the embodiment of FIG. 7.
Figure 10:
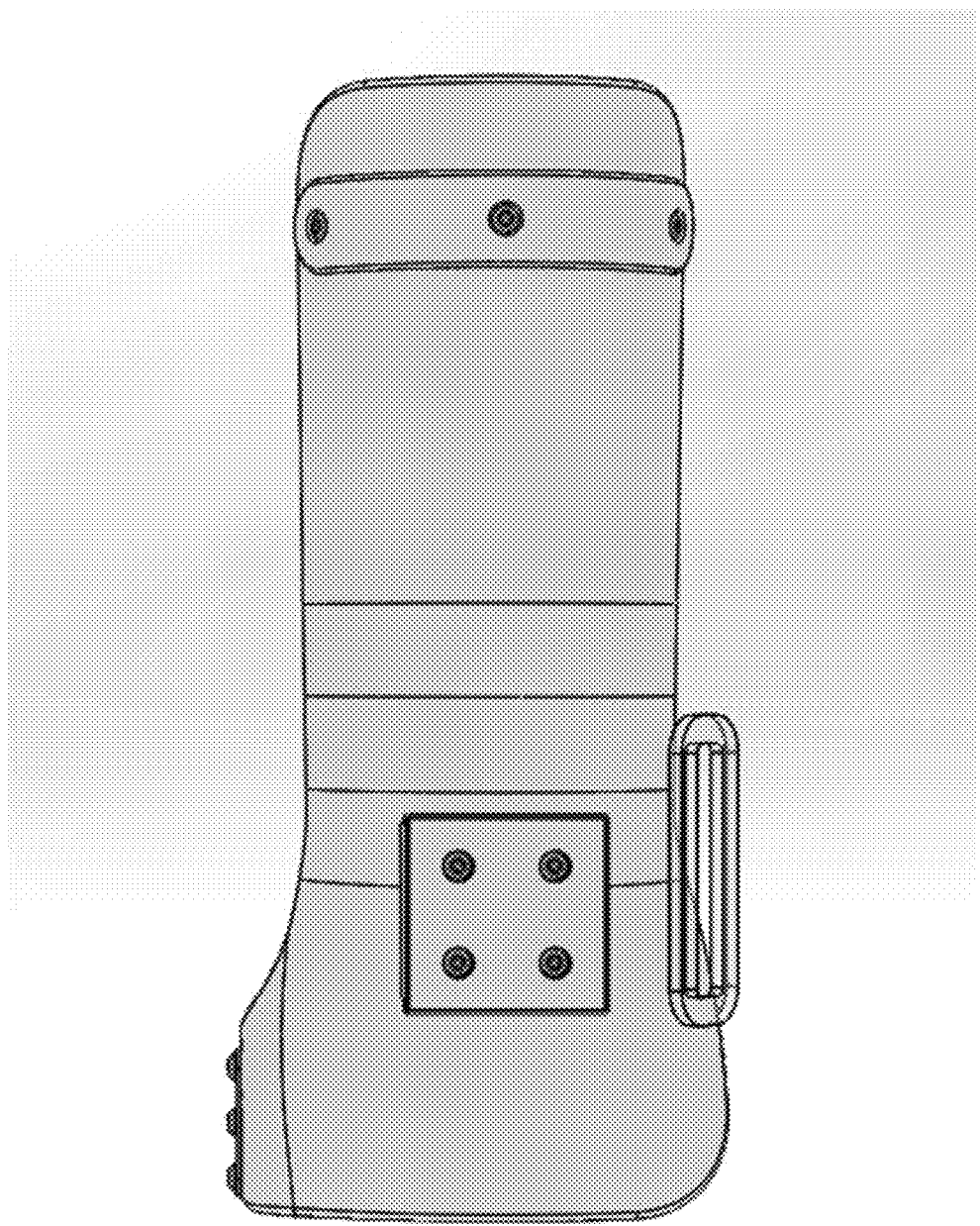
FIG. 10 includes a back view of the embodiment of FIG. 7.

Also, while above embodiments may include two restraints other embodiments may include one, three, or more restraints. Further, even with two restraints the restraints do not necessarily target the thenar eminence and hypothenar eminence, but may address other areas of the hand or human anatomy. See, for example, FIG. 6 (which has a single pawl 14 to apply pressure to metacarpal heads while continuing to avoid pressure to middle of palm).

Example 28. The apparatus of Example 27 wherein the ratchet is curved.

Example 29. The apparatus according to any of Examples 27-28 wherein the at least one ratchet tooth of the anatomical restraint includes a pawl.

Example 30. The apparatus according to any of Examples 27-29 wherein the anatomical restraint is configured to move towards the anatomical support as the ratchet tightens.

Example 31. The apparatus of Example 30 wherein in response to tightening the first ratchet, the anatomical restraint includes a surface to drive the anatomical feature laterally towards the first lateral-most edge and away from midpoint of the curved wall.

Example 32. The apparatus according to any of Examples 27-31 wherein in response to tightening the first ratchet, the anatomical restraint includes a surface to drive the anatomical feature laterally towards the first lateral-most edge.

Example 33. The apparatus according to any of Examples 27-32 comprising a coupler configured to couple the apparatus to a robot.

Example 34. The apparatus according to any of Examples 27-33 wherein the axis of rotation of the first ratchet is non-parallel to the axis of rotation of the second ratchet.

Examples 1a-7a are purposely omitted.

Example 8a. An apparatus comprising: a primary platform configured to support a hand and a forearm; a secondary platform statically coupled to the primary platform; a primary strap coupled to the primary platform, the primary strap configured to secure the forearm to the primary platform; a secondary strap coupled to the secondary platform, the secondary strap configured to secure the hand to the secondary platform; and a coupler to couple the primary platform to a robot; wherein: (a) the primary platform includes a central long axis and the secondary platform includes a central long axis, (b) the central long axis of the secondary platform is not parallel to the central long axis of the primary platform, and (c) the central long axis of the secondary platform is not orthogonal to the central long axis of the primary platform; wherein: (a) an additional axis is orthogonal to the central long axis of the primary platform, and (b) the additional axis intersects both of the primary and secondary platforms as well as a void that exists between portions of the primary and secondary platforms; wherein: (a) the secondary platform has first and second ends which oppose each other and which both intersect the central long axis of the secondary platform, (b) the second end only couples to the primary platform via the first end, and (c) the void exists between the second end and the primary platform.

The coupler may include a coupler such as the dovetail coupler 12 of FIG. 5.

The primary and second platforms may be rigid while the primary and secondary straps are flexible.

Example 9a. The apparatus of example 8a, wherein: the second end of the secondary platform is distal to the first end of the secondary platform; the central long axis of the secondary platform extends distally as the central long axis of the secondary platform extends from the first end of the secondary platform to the second end of the secondary platform.

Example 10a. The apparatus of example 8a, wherein: the secondary strap is distal to the primary strap; and the second end of the secondary platform is distal to the first end of the secondary platform.

Example 11a. The apparatus of example 10a, wherein: the primary strap has first and second ends which oppose each other, the first end of the primary strap being fixed to the primary platform; the secondary strap has first and second ends which oppose each other, the first end of the secondary strap being fixed to the secondary platform; in a first configuration: (a) the second end of the primary strap is only secured to the primary platform indirectly via the first end of the primary strap; and (b) the second end of the secondary strap is only secured to the primary platform indirectly via the first end of the secondary strap; in a second configuration: (a) the second end of the primary strap is secured directly to the primary platform and is configured to secure the forearm to the primary platform; (b) the second end of the secondary strap is secured directly to the primary platform via the first end of the secondary strap and is configured to secure the hand to the primary platform.

Example 12a. The apparatus of example 11a, wherein the second configuration is configured to secure the forearm and the hand to the primary platform such that the additional axis intersects both of the primary and second platforms and metacarpals of the hand.

Example 13a. The apparatus of example 12a, wherein: the primary platform includes first and second lateral-most opposing edges that are coupled to each other by a curved wall of the primary platform, the curved wall including a midpoint that is equidistant from the first and second lateral-most opposing edges; the first lateral-most edge, the second lateral-most edge, and the curved wall collectively form the void which is configured to receive the hand.

Example 14a. The apparatus of example 13a, wherein the void and the coupler are on opposite sides of the curved wall.

Example 15a. The apparatus of example 14a, wherein in the second configuration the second end of the primary strap is distal to the primary end of the primary strap.

Example 16a. The apparatus of example 15a, wherein the in the second configuration the primary strap is configured to directly contact a hypothenar eminence of the hand.

Example 17a. The apparatus of example 15a, wherein: the first end of the secondary platform is fixed to the primary platform via at least one coupler; and the secondary platform is configured to be decoupled from the primary platform by decoupling the at least one coupler from the primary platform.

Example 18a. The apparatus of example 17a comprising a tertiary strap configured to affix to the primary platform distal to the primary strap, wherein the tertiary strap includes a coupler to couple a sensor to the primary platform.

Example 19a. The apparatus of example 17a wherein the secondary strap includes a coupler to couple a sensor to the primary platform.

Such a sensor coupler may also exist for other embodiments such as the embodiment of FIG. 3. For instance, the sensor coupler (e.g., a hook and loop band) may couple to element 9 of FIG. 3.

Example 20a. An apparatus comprising: a primary platform configured to support a hand and a forearm; a secondary platform coupled to the primary platform; a primary strap coupled to the primary platform, the primary strap configured to secure the forearm to the primary platform; a secondary strap coupled to the secondary platform, the secondary strap configured to secure the hand to the secondary platform; and a coupler to couple the primary platform to a robot; wherein: (a) the primary strap has first and second ends which oppose each other, the first end of the primary strap being fixed to the primary platform; and (b) the secondary strap has first and second ends which oppose each other, the first end of the secondary strap being fixed to the secondary platform; wherein in a first configuration: (a) the second end of the primary strap is only secured to the primary platform indirectly via the first end of the primary strap; and (b) the second end of the secondary strap is only secured to the primary platform indirectly via the first end of the secondary strap; wherein in a second configuration: (a) the second end of the primary strap is secured directly to the primary platform and is configured to secure the forearm to the primary platform; (b) the second end of the secondary strap is secured directly to the primary platform via the first end of the secondary strap and is configured to secure the hand to the primary platform; wherein: (a) an additional axis is orthogonal to a central long axis of the primary platform, and (b) in the second configuration the additional axis intersects both of the primary and secondary platforms as well as a void that exists between portions of the primary and secondary platforms, the void being configured to receive the hand.

Thus, not all embodiments require the secondary platform be statically coupled to the primary platform. For instance, the secondary platform may have one end that couples to the primary platform via a hinge. Then, the secondary platform may "swing" open and closed to include a user's hand. The other end of the secondary platform may contact and separate from the primary platform just as the non-hinged side of a door contacts a door jam or wall depending on whether the door is closed or open.

In other embodiments the secondary platform may be separable from the primary platform on both ends of the secondary platform. For example, both ends may have a "snap fit" male/female coupling with the primary platform or some other coupler such as hook and loop couplers and the like.

A method of constructing the platform may include: (1) 3D printing a plastic primary platform, a quick-disconnect adaptor block (e.g., coupler 22), and a fabric clamp (curved bar below coupler 22 in FIG. 17), (2) form or gather polycarbonate D ring 40 and secondary platform; (3) brass press fit threaded inserts (yellow-brown) to receive bolts, (4) apply soft polyurethane foam (gray), (5) insert bolts 19, (6) adhere foam to platforms with spray glue, and (7) add synthetic leather upholstery.

In an embodiment the primary platform may include layers. For example, the primary platform may include a layer of plastic, a layer of foam, a layer of synthetic upholstery, and a layer of hook or loop fasteners. Therefore, a strap "directly" contacting the "primary platform" may include the strap directly contacting a hook or loop layer on the primary platform.

Braces addressed herein may be made in various sizes and for left or right hands.

Further, not all embodiments with a secondary platform preclude the secondary platform from extending orthogonal to a long axis of the primary platform.

In an embodiment a foot is substituted for the hand of Example 20a and a leg is substituted for the forearm of Example 20a.

Example 21a. The apparatus of example 20a, wherein the second configuration is configured to secure the forearm and the hand to the primary platform such that the additional axis intersects both of the primary and second platforms and metacarpals of the hand.

Example 22a. The apparatus of example 21a, wherein: the primary platform includes first and second lateral-most opposing edges that are coupled to each other by a curved wall of the primary platform; the first lateral-most edge, the second lateral-most edge, and the curved wall collectively form the void which is configured to receive the hand.

Example 23a. The apparatus of example 22a, wherein the void and the coupler are on opposite sides of the curved wall.

Example 24a. The apparatus of example 23a, wherein in the second configuration the second end of the primary strap is distal to the primary end of the primary strap.

Example 25a. The apparatus of example 23a, wherein the in the second configuration the primary strap is configured to directly contact a hypothenar eminence of the hand.

Example 26a. The apparatus of example 23a, wherein: the first end of the secondary platform is fixed to the primary platform via at least one coupler; and the secondary platform is configured to be decoupled from the primary platform by decoupling the at least one coupler from the primary platform.

Example 27a. The apparatus of example 26a comprising a tertiary strap configured to affix to the primary platform distal to the primary strap, wherein the tertiary strap includes a coupler to couple a sensor to the primary platform.

Example 28a. The apparatus of example 26a wherein the secondary strap includes a coupler to couple a sensor to the primary platform.

Example 29a. An apparatus comprising: a platform configured to support a hand and a forearm; a primary brace coupled to the platform, the primary brace configured to secure the forearm to the platform; a secondary brace coupled to the platform, the secondary brace configured to secure the hand to the platform; and a coupler to couple the platform to a robot; wherein: (a) the primary brace has first and second ends which oppose each other, the first end of the primary brace being fixed to the platform; and (b) the secondary brace has first and second ends which oppose each other, the first end of the secondary brace being fixed to the platform; wherein in a first configuration: (a) the second end of the primary brace is only secured to the platform indirectly via the first end of the primary brace; and (b) the second end of the secondary brace is only secured to the platform indirectly via the first end of the secondary brace; wherein in a second configuration: (a) the second end of the primary brace is secured directly to the platform and is configured to secure the forearm to the platform; (b) the second end of the secondary brace is secured directly to the platform via the first end of the secondary brace and is configured to secure the hand to the platform; wherein: (a) an additional axis is orthogonal to a central long axis of the platform, and (b) in the second configuration the additional axis intersects both of the platform and the second brace as well as a void that exists between portions of the platform and the second brace, the void being configured to receive the hand.

For instance, in FIG. 5 brace 14 may be the secondary brace and brace 41 may be the primary brace. Each may be fixed to the platform using anchors, such as bolts. However, they may also temporarily couple to the platform via a ratchet system, hook and loop system, or the like. FIG. 12 may include braces 20, 21. Neither brace needs to necessarily include a platform such as platform 18. Thus, braces may include flexible straps, rigid platforms (brace 14 of FIG. 5), and the like.

Example 30a. The apparatus of claim 29a, wherein the second configuration is configured to secure the forearm and the hand to the platform such that the additional axis intersects the platform, the secondary brace, and metacarpals of the hand.

Example 31a. The apparatus of example 30a, wherein: the platform includes first and second lateral-most opposing edges that are coupled to each other by a curved wall of the platform; the first lateral-most edge, the second lateral-most edge, and the curved wall collectively form the void which is configured to receive the hand.

Example 32a. The apparatus of example 31a, wherein the void and the coupler are on opposite sides of the curved wall.

Example 33a. The apparatus of example 32a, wherein in the second configuration the second end of the primary brace is distal to the primary end of the primary brace.

Example 34a. The apparatus of example 33a, wherein the in the second configuration the primary brace is configured to directly contact a hypothenar eminence of the hand.

Example 35a. The apparatus of example 34a, wherein: the first end of the secondary brace is fixed to the platform via at least one coupler; and the secondary brace is configured to be decoupled from the platform by decoupling the at least one coupler from the platform.

Example 36a. The apparatus of example 35a wherein the secondary brace includes a coupler to couple a sensor to the primary platform.

Example 37a. An apparatus comprising: a platform configured to support a hand and a forearm; a brace coupled to the platform, the brace configured to secure at least one of the forearm and the hand to the platform; a first coupler coupled to the brace, the first coupler configured to secure a sensor to the brace; and a second coupler to couple the platform to a robot; wherein: (a) the brace has first and second ends which oppose each other, the first end of the brace being fixed to the platform; wherein in a first configuration: (a) the second end of the brace is only secured to the platform indirectly via the first end of the brace; wherein in a second configuration: (a) the second end of the brace is secured directly to the platform and is configured to secure the forearm to the platform; wherein: (a) an additional axis is orthogonal to a central long axis of the platform, and (b) in the second configuration the additional axis intersects both of the platform and the brace as well as a void that exists between portions of the platform and the brace, the void being configured to receive the hand.

In an embodiment the second coupler is a dove tail coupler.

The foregoing description of the embodiments of the invention has been presented for the purposes of illustration and description. It is not intended to be exhaustive or to limit the invention to the precise forms disclosed. This description and the claims following include terms, such as left, right, top, bottom, over, under, upper, lower, first, second, etc. that are used for descriptive purposes only and are not to be construed as limiting. For example, terms designating relative vertical position refer to a situation where a side of a substrate is the "top" surface of that substrate; the substrate may actually be in any orientation so that a "top" side of a substrate may be lower than the "bottom" side in a standard terrestrial frame of reference and still fall within the meaning of the term "top." The term "on" as used herein (including in the claims) does not indicate that a first layer "on" a second layer is directly on and in immediate contact with the second layer unless such is specifically stated; there may be a third layer or other structure between the first layer and the second layer on the first layer. The embodiments of a device or article described herein can be manufactured, used, or shipped in a number of positions and orientations. Persons skilled in the relevant art can appreciate that many modifications and variations are possible in light of the above teaching. Persons skilled in the art will recognize various equivalent combinations and substitutions for various components shown in the Figures. It is therefore intended that the scope of the invention be limited not by this detailed description, but rather by the claims appended hereto.

What is claimed is:

1. An apparatus comprising:
a primary platform configured to support a hand and a forearm;
a secondary platform statically coupled to the primary platform;
a primary strap coupled to the primary platform; the primary strap configured to secure the forearm to the primary platform;
a secondary strap coupled to the secondary platform, the secondary strap configured to secure the hand to the secondary platform; and
a coupler to couple the primary platform to a robot;
wherein: (a) the primary platform includes a central long axis and the secondary platform includes a central long axis, (b) the central long axis of the secondary platform is not parallel to the central long axis of the primary platform, and (c) the central long axis of the secondary platform is not orthogonal to the central long axis of the primary platform;
wherein: (a) an additional axis is orthogonal to the central long axis of the primary platform, and (b) the additional axis intersects both of the primary and secondary platforms as well as a void that exists between portions of the primary and secondary platforms;
wherein: (a) the secondary platform has first and second ends which oppose each other and which both intersect the central long axis of the secondary platform, (b) the second end only couples to the primary platform via the first end, and (c) the void exists between the second end and the primary platform;
wherein: (a) the primary platform includes first and second lateral-most opposing edges that are coupled to each other by a curved wall of the primary platform, the curved wall including a midpoint that is equidistant from the first and second lateral-most opposing edges; and (b) the first lateral-most edge, the second lateral-most edge, and the curved wall collectively form the void which is configured to receive the hand.

2. The apparatus of claim 1, wherein:
the second end of the secondary platform is distal to the first end of the secondary platform;
the central long axis of the secondary platform extends distally as the central long axis of the secondary platform extends from the first end of the secondary platform to the second end of the secondary platform.

3. The apparatus of claim 1, wherein:
the secondary strap is distal to the primary strap; and
the second end of the secondary platform is distal to the first end of the secondary platform.

4. The apparatus of claim 3, wherein:
the primary strap has first and second ends which oppose each other, the first end of the primary strap being fixed to the primary platform;
the secondary strap has first and second ends which oppose each other, the first end of the secondary strap being fixed to the secondary platform;
in a first configuration: (a) the second end of the primary strap is only secured to the primary platform indirectly via the first end of the primary strap; and (b) the second end of the secondary strap is only secured to the primary platform indirectly via the first end of the secondary strap;
in a second configuration: (a) the second end of the primary strap is secured directly to the primary platform and is configured to secure the forearm to the primary platform; (b) the second end of the secondary strap is secured indirectly to the primary platform via the first end of the secondary strap and is configured to secure the hand to the primary platform.

5. The apparatus of claim 4, wherein the second configuration is configured to secure the forearm and the hand to the primary platform such that the additional axis intersects both of the primary and second platforms and metacarpals of the hand.

6. The apparatus of claim 5, wherein the void and the coupler are on opposite sides of the curved wall.

7. The apparatus of claim 6, wherein in the second configuration the second end of the primary strap is distal to the first primary end of the primary strap.

8. The apparatus of claim 7, wherein in the second configuration the primary strap is configured to directly contact a hypothenar eminence of the hand.

9. The apparatus of claim 7, wherein:
the first end of the secondary platform is fixed to the primary platform via at least one coupler; and
the secondary platform is configured to be decoupled from the primary platform by decoupling the at least one coupler from the primary platform.

10. The apparatus of claim 9 comprising a tertiary strap configured to affix to the primary platform distal to the primary strap, wherein the tertiary strap includes a coupler to couple a sensor to the primary platform.

11. The apparatus of claim 9 wherein the secondary strap includes a coupler to couple a sensor to the primary platform.

12. An apparatus comprising:
a primary platform configured to support a hand and a forearm;
a secondary platform statically coupled to the primary platform;
a primary strap coupled to the primary platform; the primary strap configured to secure the forearm to the primary platform;
a secondary strap coupled to the secondary platform, the secondary strap configured to secure the hand to the secondary platform; and
a coupler to couple the primary platform to a robot;
wherein: (a) the primary platform includes a central long axis and the secondary platform includes a central long axis, (b) the central long axis of the secondary platform is not parallel to the central long axis of the primary platform, and (c) the central long axis of the secondary platform is not orthogonal to the central long axis of the primary platform;
wherein: (a) the primary strap has first and second ends which oppose each other, the first end of the primary strap being fixed to the primary platform; and (b) the secondary strap has first and second ends which oppose each other, the first end of the secondary strap being fixed to the secondary platform;
wherein in a first configuration: (a) the second end of the primary strap is only secured to the primary platform indirectly via the first end of the primary strap; and (b) the second end of the secondary strap is only secured to the primary platform indirectly via the first end of the secondary strap;

wherein in a second configuration: (a) the second end of the primary strap is secured directly to the primary platform and is configured to secure the forearm to the primary platform; (b) the second end of the secondary strap is secured indirectly to the primary platform via the first end of the secondary strap and is configured to secure the hand to the primary platform wherein: (a) an additional axis is orthogonal to a central long axis of the primary platform, and (b) in the second configuration the additional axis intersects both of the primary and secondary platforms as well as a void that exists between portions of the primary and secondary platforms, the void being configured to receive the hand;

wherein: (a) the primary platform includes first and second lateral-most opposing edges that are coupled to each other by a curved wall of the primary platform, the curved wall including a midpoint that is equidistant from the first and second lateral-most opposing edges; and (b) the first lateral-most edge, the second lateral-most edge, and the curved wall collectively form the void which is configured to receive the hand.

13. The apparatus of claim 12, wherein the second configuration is configured to secure the forearm and the hand to the primary platform such that the additional axis intersects both of the primary and second platforms and metacarpals of the hand.

* * * * *